United States Patent
Hu

(10) Patent No.: US 9,206,194 B2
(45) Date of Patent: Dec. 8, 2015

(54) HALICHONDRIN B ANALOGS

(71) Applicant: Eisai R&D Management Co., Ltd., Tokyo (JP)

(72) Inventor: Yongbo Hu, Malden, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/058,742

(22) Filed: Oct. 21, 2013

(65) Prior Publication Data

US 2014/0163244 A1  Jun. 12, 2014

Related U.S. Application Data

(62) Division of application No. 12/936,056, filed as application No. PCT/US2009/039432 on Apr. 3, 2009, now Pat. No. 8,598,373.

(60) Provisional application No. 61/071,111, filed on Apr. 11, 2008, provisional application No. 61/042,643, filed on Apr. 4, 2008.

(51) Int. Cl.
*C07D 321/00* (2006.01)
*C07D 493/22* (2006.01)

(52) U.S. Cl.
CPC .................................. *C07D 493/22* (2013.01)

(58) Field of Classification Search
USPC ......................................................... 549/348
See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 5,451,573 A | 9/1995 | Hemmerle et al. | |
| 6,214,865 B1 | 4/2001 | Littlefield et al. | |
| 6,365,759 B1 | 4/2002 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,097,648 B2 | 1/2012 | Littlefield et al. | |
| 8,148,554 B2 | 4/2012 | Seletsky et al. | |
| 8,203,010 B2 | 6/2012 | Endo et al. | |
| 8,350,067 B2 | 1/2013 | Endo et al. | |
| 8,445,701 B2 | 5/2013 | Austad et al. | |
| 8,598,373 B2 * | 12/2013 | Hu ................................ 549/348 |
| 8,618,313 B2 | 12/2013 | Benayoud et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2011/0172446 A1 | 7/2011 | Littlefield et al. | |
| 2011/0184190 A1 | 7/2011 | Endo et al. | |
| 2012/0029213 A1 | 2/2012 | Austad et al. | |
| 2012/0095242 A1 | 4/2012 | Chase et al. | |
| 2012/0309988 A1 | 12/2012 | Austad et al. | |
| 2013/0123519 A1 | 5/2013 | Endo et al. | |
| 2013/0237711 A1 | 9/2013 | Benayoud et al. | |

FOREIGN PATENT DOCUMENTS

| | | |
|---|---|---|
| EP | 0572109 A1 | 12/1993 |
| JP | 2002-518384 A | 6/2002 |
| WO | WO-93/17690 A1 | 9/1993 |
| WO | WO-99/65894 A1 | 12/1999 |
| WO | WO-2005/118565 A1 | 12/2005 |
| WO | WO-2006/076100 A2 | 7/2006 |
| WO | WO-2009/046308 A1 | 4/2009 |
| WO | WO-2009/064029 A1 | 5/2009 |
| WO | WO-2009/124237 A1 | 10/2009 |
| WO | WO-2011/094339 A1 | 8/2011 |
| WO | WO-2012/147900 A1 | 11/2012 |

OTHER PUBLICATIONS

U.S. Appl. No. 14/096,549, Chase et al.
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-64 (1992).
Aicher, Thomas Daniel, Thesis, Chapter 4, "Synthetic studies towards halichondrin B," Doctor of Philosophy in Chemistry, Harvard University, 35-54 (1990).
Alley et al. "Comparison of the relative efficacies and toxicities of Halichondrin B analogues," Proceedings of the AACR-NCI-EORTC Conference on Molecular Targets and Cancer Therapeutics. C230:257 (2005).
Anderson, "Developing processes for crystallization-induced asymmetric transformation," Org Process Res Dev. 9:800-13 (2005).
Austad et al., "Commercial manufacture of Halaven®: chemoselective transformations en route to structurally complex macrocyclic ketones," Synlett. 24 (2013). Supporting Information, (13 pages.).
Austad et al., "Commercial manufacture of Halaven®: chemoselective transformations en route to structurally complex macrocyclic ketones," Synlett. 24:333-7 (2013).
Austad et al., "Process development of Halaven®: synthesis of the C14-C35 fragment via iterative Nozaki-Hiyama-Kishi reaction—Williamson ether cyclization," Synlett. 24:327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem 266(24):15882-89 (1991).
Bernet et al., "Carbocyclische verbindungen aus monosacchariden. Umsetzungen in der glucosereihe," Hely Chim Acta. 62:1990-2016 (1979).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20) → C(36) precursor," Tetrahedron Lett. 36(39):7023-6 (1995).
Burke et al., "Synthesis of a C(22)—C(34) Halichondrin B precursor via ring opening—double ring closing metathesis," J Org Chem. 63:8626-7 (1998).

(Continued)

*Primary Examiner* — Nizal Chandrakumar
(74) *Attorney, Agent, or Firm* — Clark & Elbing LLP

(57) ABSTRACT

The invention includes halichondrin B analogs having pharmaceutical activity; in some cases, crystalline forms thereof, and in some cases, halichondrin B analogs having a further utility as synthetic intermediate.

7 Claims, 21 Drawing Sheets

(56) References Cited

OTHER PUBLICATIONS

Burke et al., "Synthesis of a C(22) → C(34) Halichondrin precursor via a double dioxanone-to-dihydropyran rearrangement," Tetrahedron Lett. 32(32):3961-4 (1991).
Burke et al., "Synthetic studies toward complex polyether macrolides of marine origin," Spec Publ R Soc Chem. 198:(Anti-Infectives) 73-85 (1997).
Chase et al., "Process development of Halaven®: Synthesis of the C1-C13 fragment from D-(−)-Gulono-1, 4-lactone," Synlett. 24:323-326 (2013).
Chen et al., "Ni(II)/Cr(II)-mediated coupling reaction: An asymmetric process," J Org Chem. 60:5386-7 (1995).
Choi et al., "Assymmetric Ni(II)/Cr(II)-mediated coupling reaction: catalytic process," Org Lett.4(25):4435-8 (2002).
Choi et al., "Synthetic studies on the marine natural product Halichondrins," Pure Appl Chem. 75(1):1-17 (2003).
Cooper et al., "Total Synthesis of Halichondrin B from common sugars: an F-ring intermediate from D-glucose and efficient construction of the C1 to C21 segment," Tetrahedron Lett. 34(51):8193-8196 (1993).
Dabydeen et al. "Comparison of the activities of the truncated Halichondrin B analog NSC 707389 (E7389) with those of the parent compound and a proposed binding site on tubulin" Mol Pharmacol. 70(6):1866-75 (2006).
Dong et al. "New syntheses of E7389 C14-C35 and halichondrin C14-C38 building blocks: reductive cyclization and oxy-michael cyclization approaches," J Am Chem Soc. 131:15642-6 (2009).
Duan et al., "Synthetic studies on halichondrins: a new practical synthesis of the C.1-C.12 segment," Tetrahedron Lett. 34(47):7541-7544 (1993).
Flemming et al., "Nitrile anion cyclizations," Tetrahedron. 58:1-23 (2002).
Hirata et al., "Halichondrins—antitumor polyether macrolides from a marine sponge," Pure Appl Chem. 58(5):701-710 (1986).
Hon et al., "Efficient synthesis of 2,3-trans-tetrahydropyrans and oxepanes: rearrangement-ring expansion of cyclic ethers having a chloromethanesulfonate," Tetrahedron Lett. 40:2145-2148 (1999).
Horita et al., "Research on anti-tumor active site of marine source natural product, Halichondrin B.," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled Iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isssolated from a marine sponge. 9. Synthesis of the C16-C36 unit via stereoselective construction of the D and E rings," Chem Pharm Bull. 46(8):1199-1216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
International Preliminary Report on Patentability from International Application No. PCT/US2009/039432 dated Oct. 5, 2010.
International Search Report from International Application No. PCT/US2009/039432, mailed Jun. 22, 2009.
Jackson et al., "A total synthesis of norhalichondrin B," Angew Chem Int Ed. 48:2346-2350 (2009).
Jackson et al., "The halichondrins and E7389," Chem Rev 109:3044-3079 (2009).
Jiang et al., "A novel route to the F-ring of Halichondrin B. Diastereoselection in Pd(0)-mediated meso and C2 diol desymmetrization," Org Lett., 4(20):3411-3414 (2002).
Jiang et al., "A practical synthesis of the F-ring of Halichondrin B via ozonolytic desymmetrization of a C2-symmetric dihydroxycyclohexene," J Org Chem. 68:1150-1153 (2003).
Kim et al., "New syntheses of E7389 C14-C35 and Halichondrin C14-C38 building blocks: double-inversion approach" J Am Chem Soc. 131:15636-4 (2009).
Kurosu et al., "Fe/Cr- and Co/Cr-mediated catalytic asymmetric 2-Haloallylations of aldehydes," J Am Chem Soc. 126:12248-9 (2004).
Mattocks, "371. Novel reactions of some alpha-acyloxy acid chlorides," J Chem Soc. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Newman, "Drug evaluation: eribulin, a simplified ketone analog of the tubulin inhibitor Halichondrin B, for the potential treatment of cancer," Curr Opin Invest Drugs. 8:1057-1066 (2007).
RN 185411-09-0 CN L-arabino-D-allo-Dodeconic acid, 3,7:6,10-dianhydro-8,9-O-cyclohexylidene-2,4,5-trideoxy-, methyl ester Entry Date: Entered STN: Jan. 28, 1997.
RN 546141-26-8 CN 1,2-Propanediol, 3-[(2R,3R,4R,5S)-tetrahydro-3-hydroxy-4-[(phenylsulfonyl)methyl]-5-(2-propen-1-yl)-2-furanyl]-, 1,2-dibenzoate, (2S)-(9CI) Entry Date: Entered STN: Jul. 11, 2003.
RN 546141-39-3 CN 1,2-Propanediol, 3-[(2R,3R,4S,5S)-tetrahydro-3-methoxy-4-[(phenylsulfonyl)methyl]-5-(2-propen-1-yl)-2-furanyl]-, 1,2-dibenzoate, (2S)-(9 CI) Entry Date: Entered STN: Jul. 11, 2003.
RN 546141-40-6 CN 1,2-Propanediol, 3-[(2R,3R,4S,5S)-tetrahydro-3-methoxy-4-[(phenylsulfonyl)methyl]-5-(2-propen-1-yl)-2-furanyl](2S)—ED Entered STN: Jul. 11, 2003.
Sakamoto et al., "Stereoselective ring expansion via bicyclooxonium Ion. A novel approach to oxocanes," Org Lett. 4(5):675-678 (2002).
Schreiber, "Hydrogen transfer from tertiary amines to trifluoroacetic anhydride," Tetrahedron Lett. 21:1027-1030 (1980).
Seletsky et al. "Structurally simplified macrolactone analogues of halichondrin B," Bioorg Med Chem Lett. 14:5547-50 (2004).
Stamos et al., "A mild preparation of vinyliodides from vinylsilanes," Tetrahedron Lett. 37(48): 8647-8650 (1996).
Stamos et al., "New synthetic route to the C.14-C.38 segment of Halichondrins," J Org Chem. 62:7552-7553 (1997).
Stamos et al., "Synthetic studies on Halichondrins: a practical synthesis of the C.1-C.13 segment," Tetrahedron Lett. 37(48): 8643-8646 (1996).
Stamos, D.P., et al., "Ni(II)/Cr(II)-mediated coupling reaction: beneficial effects of 4-tert-butylpyridine as an additive and development of new and improved workup procedures," Tetrahedron Lett., 38(36):6355-6358 (1997).
Tokunaga et al., "Asymmetric catalysis with water: efficient kinetic resolution of terminal epoxides by means of catalytic hydrolysis," Science. 277:936-938 (1997).
Towle et al. "Halichondrin B macrocyclic ketone analog E7389: medicinal chemistry repair of lactone ester instability generated during structural simplification to clinical Candidate" Annual Meeting of the American Association for Cancer Research, Apr. 6-10, 2002, 5721.
Towle et al. "In vitro and in vivo anticancer activities of synthetic macrocyclic ketone analogues of Halichondrin B" Cancer Res. 61:1013-1021 (2001).
Uemura et al., "Norhalichondrin A: an antitumor polyether macrolide from a marine sponge," J Am Chem Soc. 107:4796-4798 (1985).

(56) References Cited

OTHER PUBLICATIONS

Vahdat et al., "Phase II study of eribulin mesylate, a Halichondrin B analog, in patients with metastatic breast cancer previously treated with an anthracycline and a taxane," J Clin Oncol. 27(18):2954-2961 (2009).

Wan et al., "Asymmetric NI(II)/Cr(II)-mediated coupling reaction: Stoichiometric process," Org Lett. 4(25):4431-4434 (2002) Supporting Information, 8 pages.

Wan et al., "Asymmetric Ni(II)/Cr(II)-mediated coupling reaction: Stoichiometric process," Org Lett. 4(25):4431-4434 (2002).

Wang et al. "Structure-activity relationships of Halichondrin B analogues: Modifications at C.30-C.38" Bioorg Med Chem Lett. 10:1029-1032 (2000).

Xie et al., "Synthesis of the C20-C26 building block of Halichondrins via a regiospecific and stereoselective SN2' reaction," Org Lett. 4(25): 4427-4429 (2002).

Yang et al., "Second generation synthesis of C27-C35 building block of E7389, a synthetic Halichondrin analogue," Org Lett. 11(20): 4516-4519 (2009).

Yu et al., "New synthetic route to the C.14-C.21 fragment of Halichondrin B," Book of Abstracts. 219th ACS National Meeting, San Francisco, CA, (Mar. 26-30, 2000).

Yu et al., Discovery of E7389 a fully synthetic macrocyclic ketone analog of Halichondrin B. *Anticancer Agents from Natural Product*. CRC Press, 241-265 (2005).

Zheng et al., "Macrocyclic ketone analogues of Halichondrin B," Bioorg Med Chem Lett. 14: 5551-5554 (2004).

Zheng, W. et al. "Synthetic macrocyclic ketone analogs of halichondrin B: structure-activity relationships" Proceedings of the American Association for Cancer Research, 41:301(#1915) (2000).

U.S. Appl. No. 14/250,086, Fang et al.

"Chemistry Handbook, Applied Chemistry, 6th Edition," Maruzen Publishing Co., Ltd. p. 178 (2003).

English Translation of an Office Action issued for Japanese Patent Application No. 2011-503,203, dispatched Dec. 3, 2013 (3 pages).

English Translation of "Chemistry Handbook, Applied Chemistry, 6th Edition," Maruzen Publishing Co., Ltd. p. 178 (2003), received Oct. 6, 2014 (3 pages).

\* cited by examiner

HALICHONDRIN B ANALOGS

RELATED APPLICATIONS

This application is a divisional of U.S. application Ser. No. 12/936,056, filed Nov. 4, 2010 now U.S. Pat. No. 8,598,373, which is the National Stage of International Application No. PCT/US2009/039432, filed Apr. 3, 2009, which claims the benefit of priority to U.S. Provisional Application No. 61/042,643, filed Apr. 4, 2008, and U.S. Provisional Application No. 61/071,111, filed Apr. 11, 2008, all of which are herein incorporated by reference in their entirety.

FIELD OF THE INVENTION

This invention relates to halichondrin B analogs having pharmaceutical activity. In some embodiments, the analogs have a crystalline form and/or have a further utility as a synthetic intermediate in the synthesis of the halichondrin B analog E7389, a compound having potent anticancer properties.

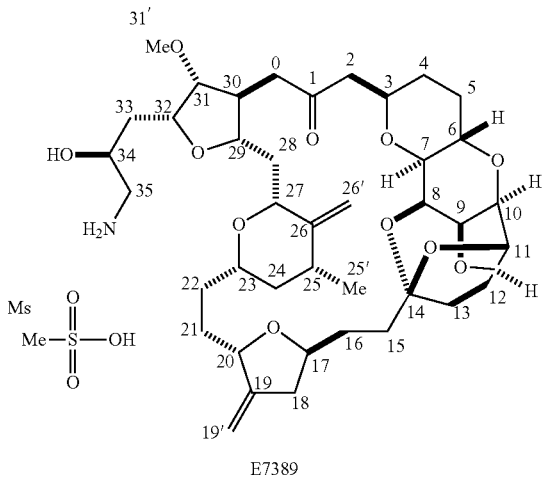

E7389

BACKGROUND OF THE INVENTION

Halichondrin B, a potent anticancer agent, was first isolated from the marine sponge *Halichondria okadai*. It is also found in *Axinella* sp., *Phakellia carteri*, and *Lissondendryx* sp. Halichondrin B has demonstrated in vitro inhibition of tubulin polymerization, microtubule assembly, beta$^S$-tubulin crosslinking, GTP and vinblastine binding to tubulin, and tubulin-dependent GTP hydrolysis. It has also shown in vitro and in vivo anticancer activity.

Aicher, et al. published a total synthesis of halichondrin B in 1992. See Aicher, T. D. et al., *J. Am. Chem. Soc.* 114:3162-3164, and Zheng, W. J. et al., *J. Bioorg. Med. Chem. Lett.* 2004, 14, 5551. The syntheses of halichondrin B and various analogs have also been described in U.S. Pat. Nos. 6,214,865; 6,365,759; 6,469,182; and 6,653,341; in U.S. published patent applications 2004/0198806 and 2006/0104984; and in PCT published application WO 2005/118565, all of which are herein incorporated by reference in their entirety.

SUMMARY OF THE INVENTION

This invention relates to halichondrin B analogs having pharmaceutical activity. The analogs have a crystalline form and/or have a further utility as a synthetic intermediate in the synthesis of the halichondrin B analog E7389, a compound having potent anticancer properties. Accordingly, the invention relates to a crystalline form of ER-076349 monohydrate; a crystalline form of ER-809681; the compound ER-820057 or a crystalline form of ER-820057; the compound ER-818906 or a crystalline form of ER-818906; the compound ER-819531 or a crystalline form of ER-819531; and the compound ER-111197 or a crystalline form of ER-111197. The invention also relates to pharmaceutical compositions containing these compounds, and methods of treating cancer by administering the compounds.

BRIEF DESCRIPTION OF FIGURES

FIG. 1-B is the crystal packing diagram of ER-076349 monohydrate along the b-axis.

FIG. 1-C is the X-ray Powder Diffraction (XRPD) pattern of ER-076349 monohydrate crystallized from isopropyl alcohol.

FIG. 1-D is a plot of XRPD patterns of ER-076349 monohydrate from various solvents.

FIG. 1-E is a plot of the DSC of ER-076349 monohydrate crystallized from ethanol.

FIG. 1-F is a plot of the DSC of ER-076349 monohydrate crystallized from isopropanol.

FIG. 1-G is a plot of the DSC of ER-076349 monohydrate crystallized from propionitrile.

FIG. 2-B is the crystal packing diagram of ER-818906 monoacetonitrile solvate along the c-axis.

FIG. 2-C is the XRPD pattern of ER-818906 (epi-C20 diol) mono-acetonitrile solvate.

FIG. 3-B is the crystal packing diagram of ER-819531 (epi-C23 diol) monohydrate along the b-axis.

FIG. 3-C is the XRPD pattern of ER-819531 (epi-C23 diol)

FIG. 5-B is the crystal packing diagram of ER-111197 (epi-C34 diol) monohydrate along the a-axis. FIG. 5-C is the XRPD spectrum of ER-111197.

FIG. 6-B is the crystal packing diagram of ER-809681 (epoxide) along the b-axis.

FIG. 6-C is the XRPD pattern of ER-809681 (epoxide).

FIG. 6-D is the calculated XRPD pattern of ER-809681 (epoxide).

DETAILED DESCRIPTION OF INVENTION

Figure 1A:
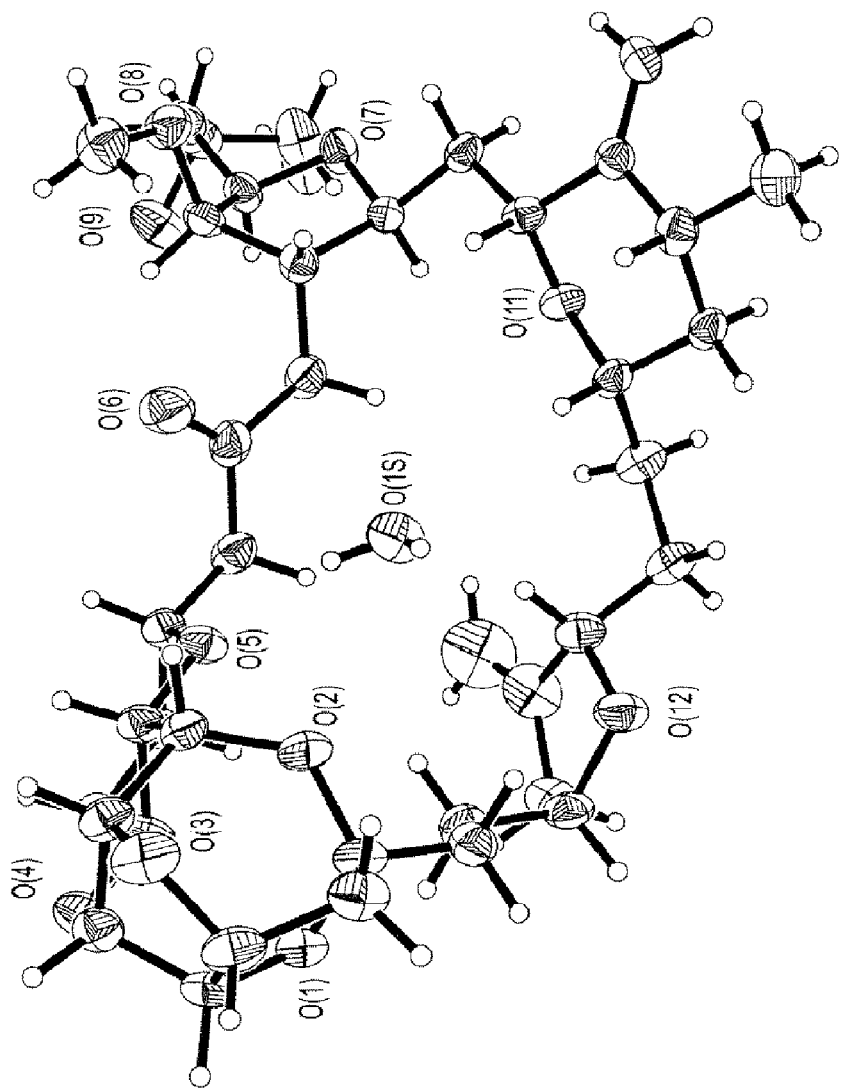
FIG. 1-A is an ORTEP drawing of the single crystal structure of ER-076349-00 monohydrate.
Figure 1B:
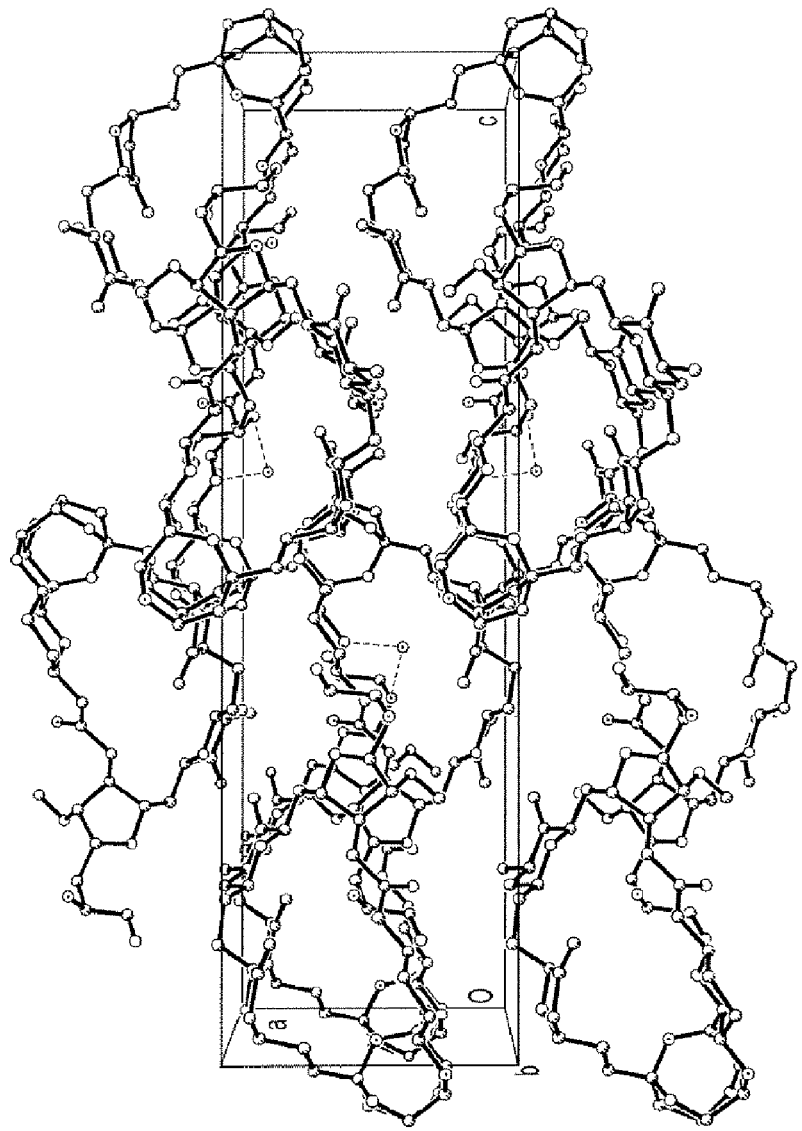
Figure 1C:
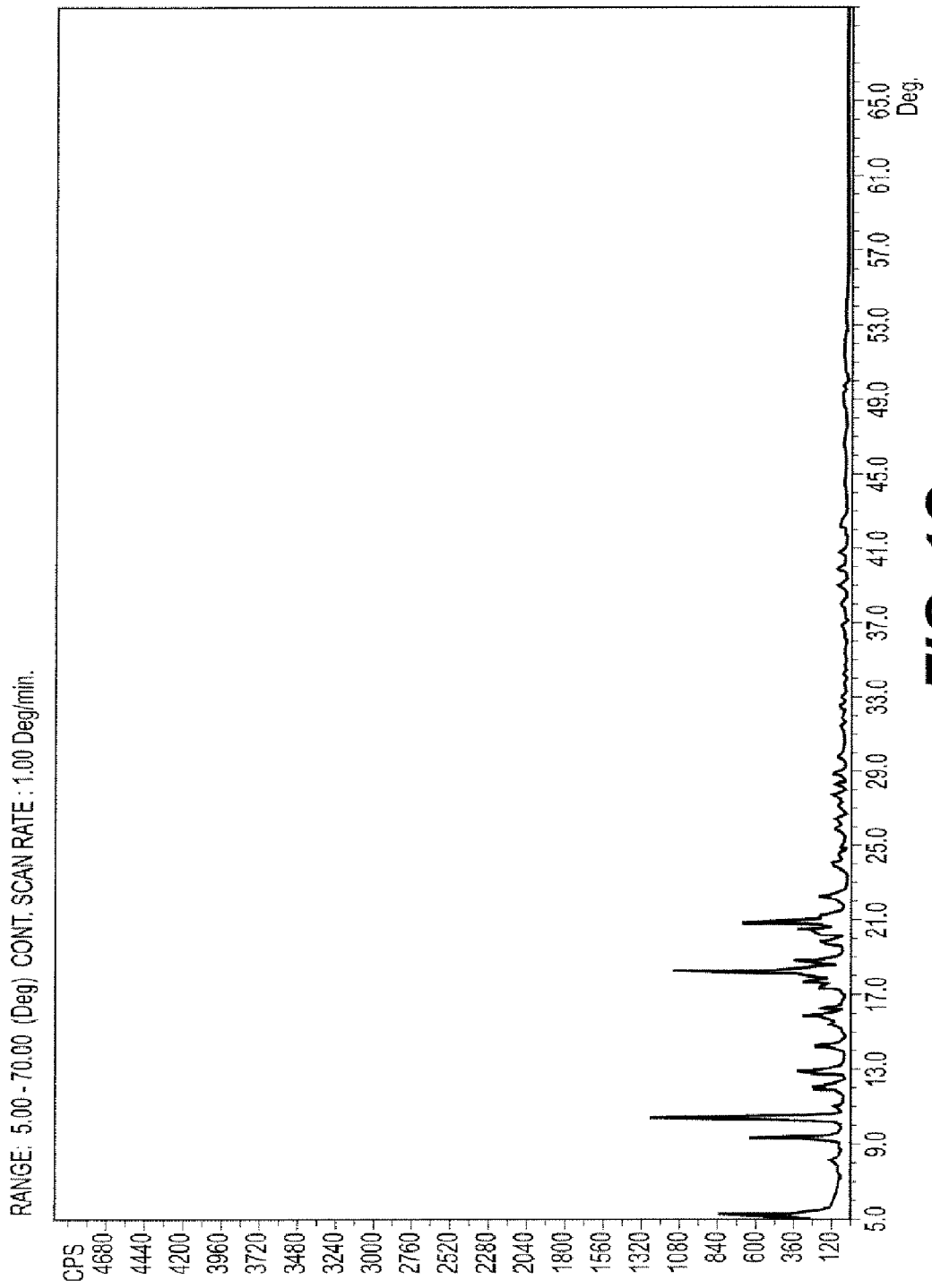
Figure 1D:
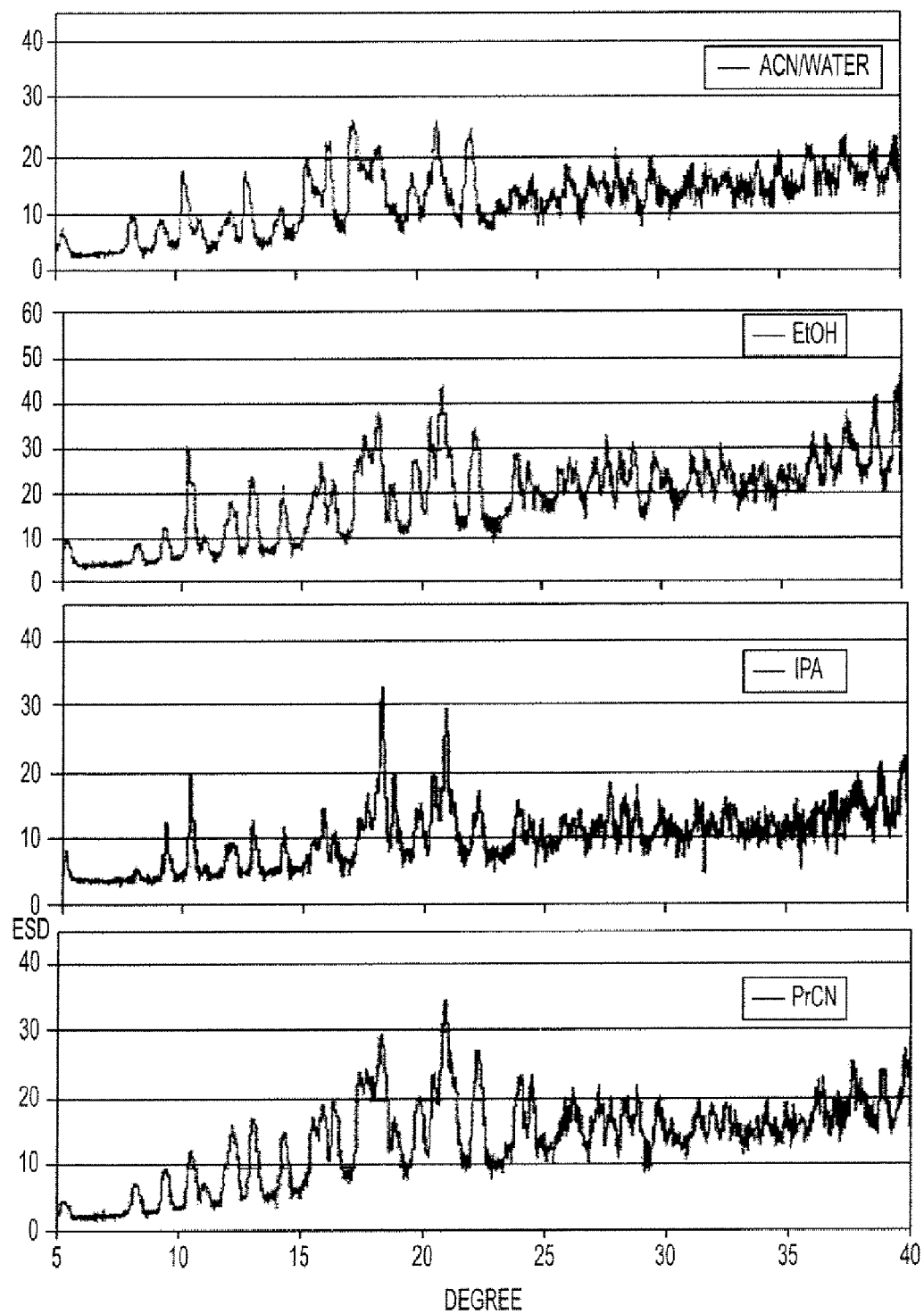
Figure 1E:
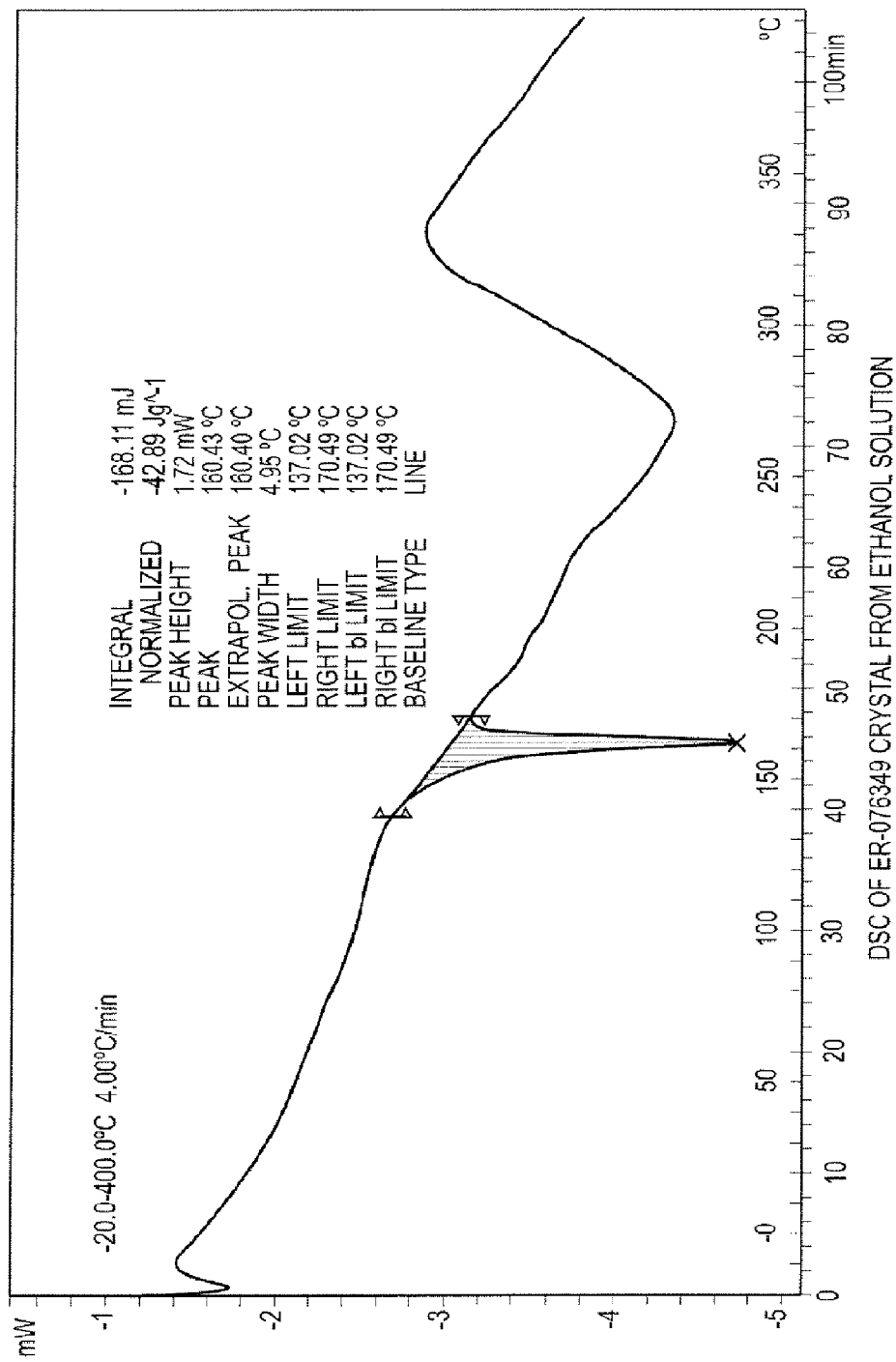
Figure 1F:
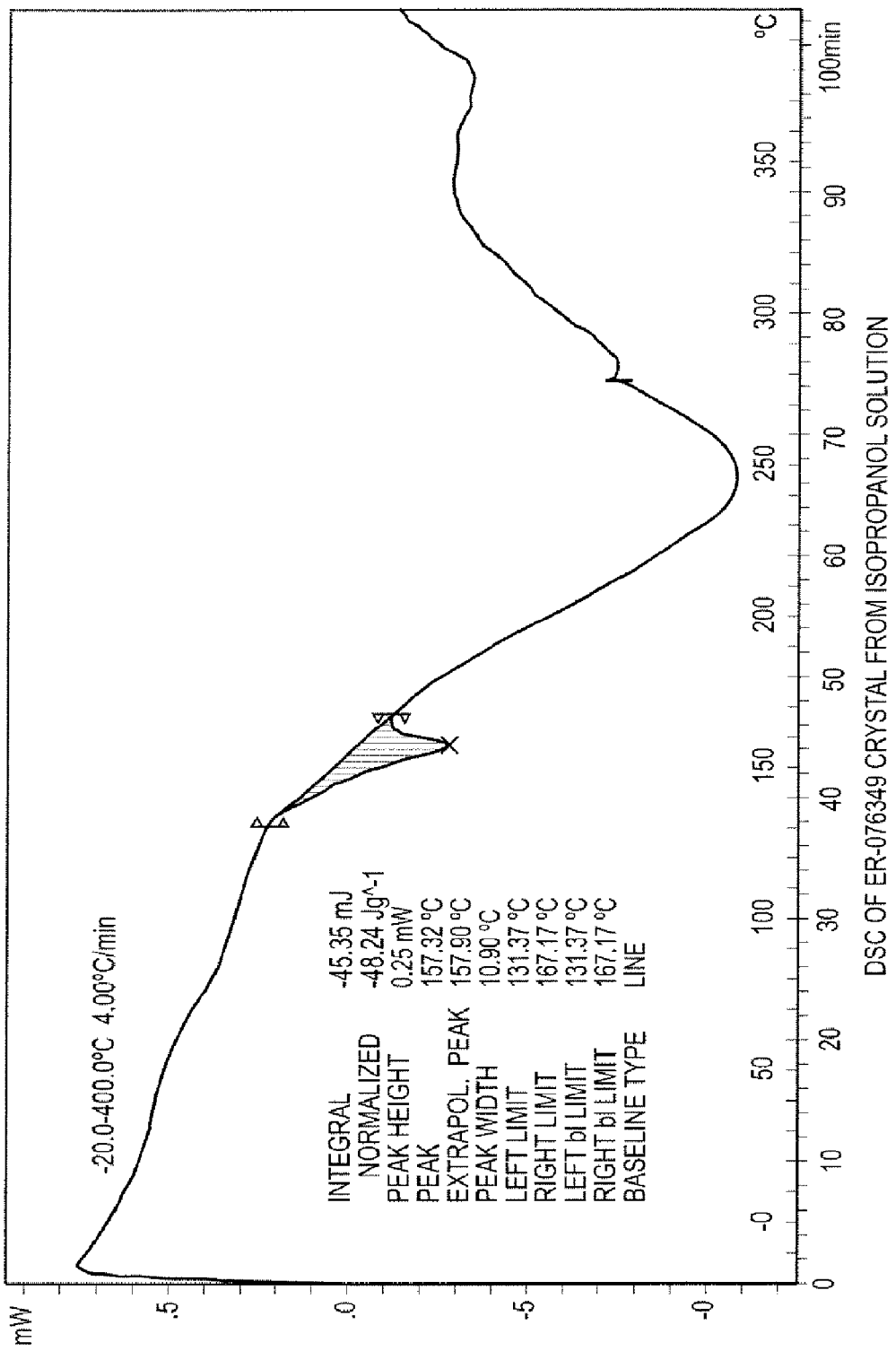
Figure 1G:
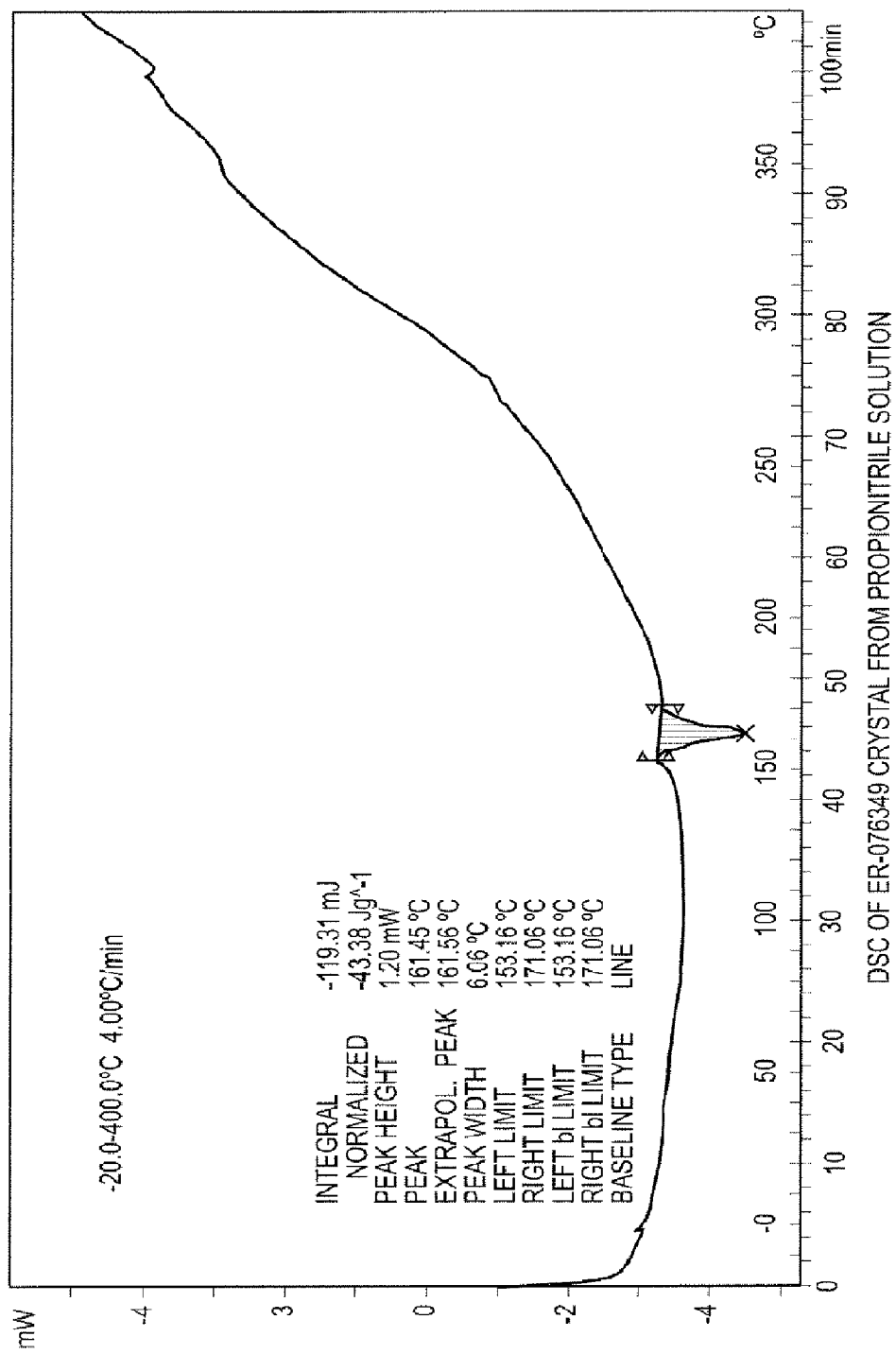

As described in U.S. Pat. No. 6,214,865, the halichondrin B analog, ER-086526 (identified as compound B-1939), is a potent antitumor agent. ER-086526 is prepared from an intermediate diol compound, ER-076349 (identified as compound B-1793). U.S. Pat. No. 6,214,865 describes the preparation of ER-076349 (B-1793) as well as its use in the preparation of several other halichondrin B analogs.
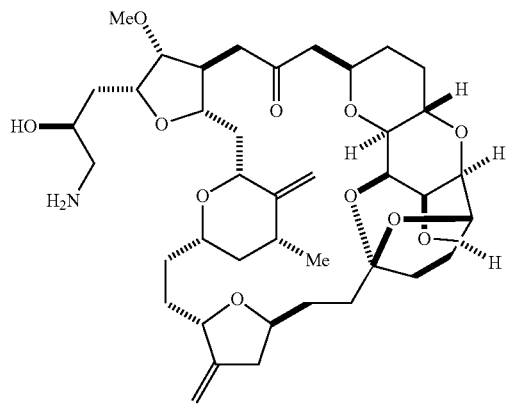
ER-086526
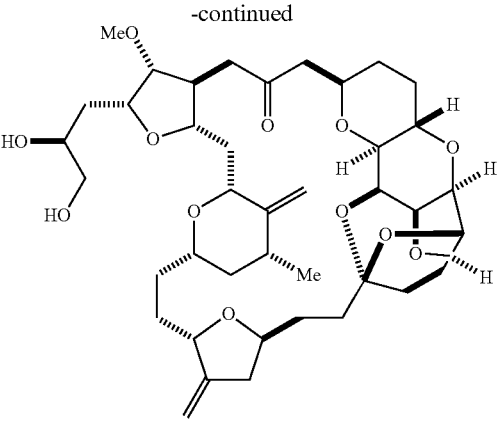
ER-076349
An alternative synthetic route to ER-086526 via ER-076349 is described in PCT published application WO 2005/118565. According to WO 2005/118565, ER-076349 is converted into ER-086526 as follows:
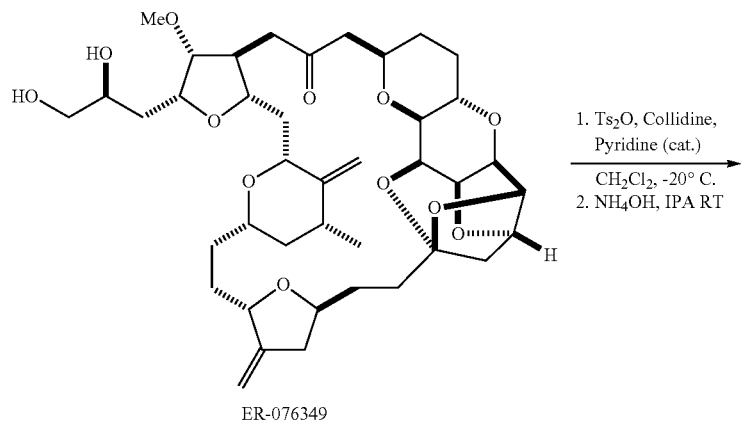
ER-076349
1. Ts$_2$O, Collidine, Pyridine (cat.)
   CH$_2$Cl$_2$, −20° C.
2. NH$_4$OH, IPA RT
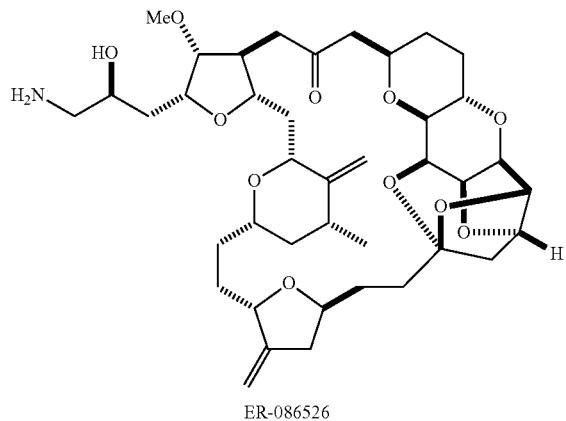
ER-086526

In the WO 2005/118565 process, ER-076349 is reacted to form a tosylate in situ, ER-082892, which then converts to an epoxide in situ, ER-809681, before forming ER-086526, as shown in the following scheme:

pared and unwanted by-products or impurities can be carried forward from earlier steps. Often filtration, separation, and/or purification steps are introduced to remove unwanted by-products or impurities. Incorporating such steps not only can increase costs but can decrease the overall yield of the synthesis. Having a crystalline intermediate within a multi-step synthesis can address these problems. A crystalline intermediate provides certain advantages—a high purity intermediate can reduce the need for other purification steps and reduce the cost of the synthetic process. In the preparation of ER-086526, having crystalline ER-076349 monohydrate as a

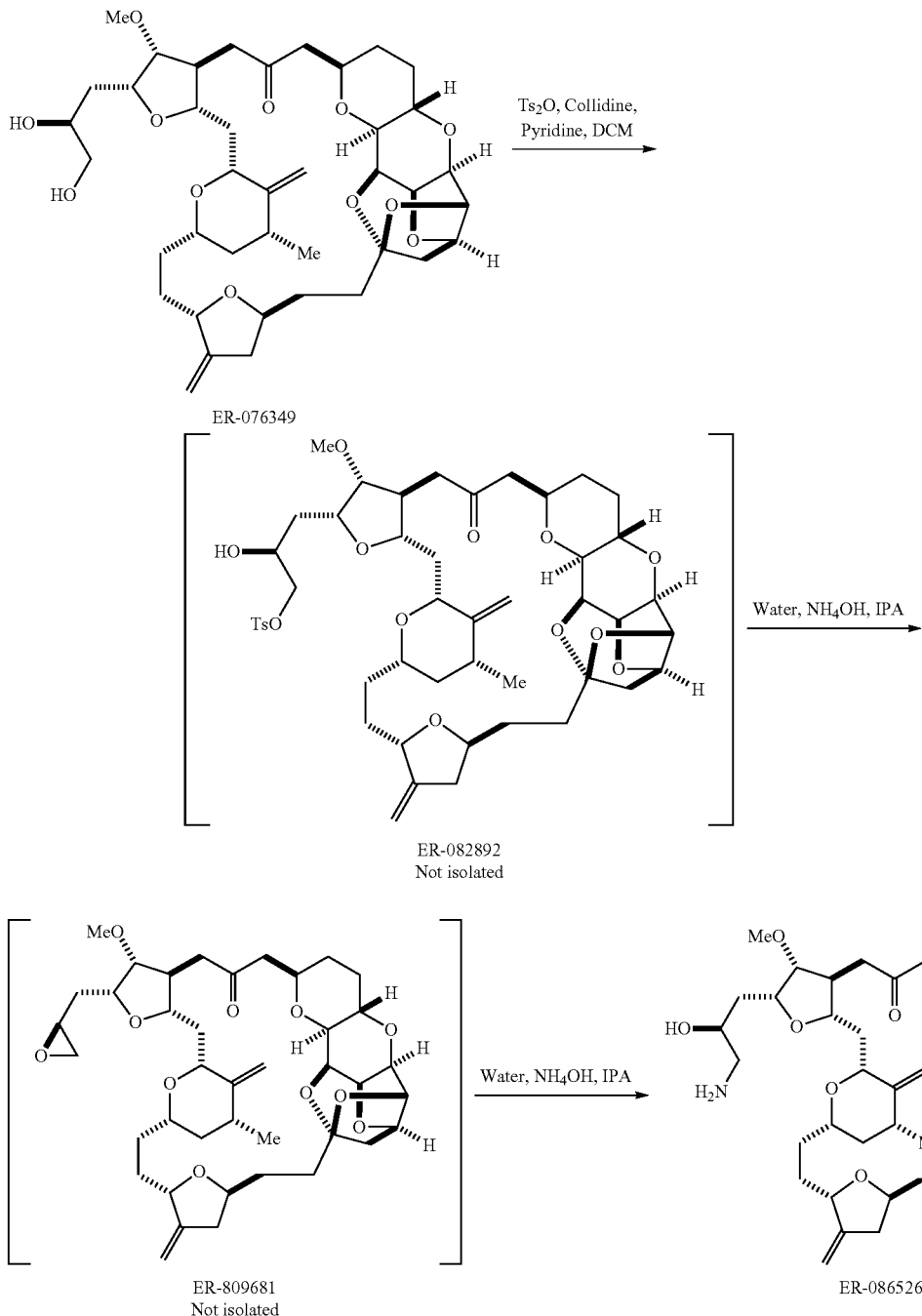

ER-076349 crystallizes from various solvents as a monohydrate. The epoxide, ER-809681, may also be isolated as a crystalline compound. Crystalline ER-076349 monohydrate (example 1) and crystalline ER-809681 (example 6) represent separate embodiments of this invention.

In multi-step syntheses, such as those described in U.S. Pat. No. 6,214,865 and WO 2005/118565, intermediates are prehigh purity intermediate allows separation from its C25 epimer. In the bulk crystalline ER-076349, the amount of the C25 epimer is generally below 0.1 wt %.

This invention also relates to crystalline forms of certain diastereomers of ER-076349. One or more diastereomers are common impurities occurring in the multi-step synthesis of compounds having several chiral carbon atoms. It is useful to characterize the various diastereomers in order to identify the epimeric impurities which occur, or might occur, in the preparation of the desired compound. Identifying an epimeric impurity can lead to process improvements to reduce, avoid, quantify, or remove the impurity. Crystalline forms of the various epimers allows for specific characterization of the particular epimer and its identification in the synthesis. In addition, crystallization of a particular epimer can be a means of removing it and thereby purifying the desired compound. Crystalline forms of epimers of ER-076349 address these needs in the synthesis of ER-086526. Crystalline forms of the following compounds, related to ER-076349, represent further embodiments of this invention: ER-809681; ER-820057; ER-818906; ER-819531; and ER-111197, all of which exhibit anti-cancer activity. This group of compounds and crystalline forms of the compounds is collectively referred to as halichondrin B analogs and individually referred to as a halichondrin B analog for this purposes of this disclosure.

There are numerous types of anti-cancer approaches that can be used in conjunction with halichondrin B analog treatment, according to the invention. These include, for example, treatment with chemotherapeutic agents (see below), biological agents (e.g., hormonal agents, cytokines (e.g., interleukins, interferons, granulocyte colony stimulating factor (G-CSF), macrophage colony stimulating factor (M-CSF), and granulocyte macrophage colony stimulating factor (GM-CSF)), chemokines, vaccine antigens, and antibodies), anti-angiogenic agents (e.g., angiostatin and endostatin), radiation, and surgery.

The methods of the invention can employ these approaches to treat the same types of cancers as those for which they are known in the art to be used, as well as others, as can be determined by those of skill in this art. Also, these approaches can be carried out according to parameters (e.g., regimens and doses) that are similar to those that are known in the art for their use. However, as is understood in the art, it may be desirable to adjust some of these parameters, due to the additional use of a halichondrin B analog with these approaches. For example, if a drug is normally administered as a sole therapeutic agent, when combined with a halichondrin B analog, according to the invention, it may be desirable to decrease the dosage of the drug, as can be determined by those of skill in this art. Examples of the methods of the invention, as well as compositions that can be used in these methods, are provided below.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with halichondrin B treatment, according to the invention. Specific, non-limiting examples of these classes of drugs, as well as cancers that can be treated by their use, are as follows.

Antimetabolite drugs that halichondrin B analogs can be used with include, e.g., methotrexate, purine antagonists (e.g., mercaptopurine, thioguanine, fludarabine phosphate, cladribine, and pentostatin), and pyrimidine antagonists (e.g., gemcitabine, capecitabine, fluorouracil (e.g., 5-FU), cytarabine, and azacitidine). Use of these agents to treat particular types of cancers is well known in the art, and these agents can be used in combination with halichondrin B analogs to treat these and other types of cancers. As specific, non-limiting examples, a halichondrin B analog can be used with gemcitabine in the treatment of non-small cell lung carcinoma, pancreatic cancer, or metastatic breast cancer. In an additional example, a halichondrin B analog can be used in conjunction with capecitabine in the treatment of breast or colorectal cancers.

As is noted above, another class of chemotherapeutic drugs with which halichondrin B analogs can be used includes anticancer antibiotics. These include, for example, anthracyclines (e.g., doxorubicin, epirubicin, daunorubicin, and idarubicin), adriamycin, dactinomycin, idarubincin, plicamycin, mitomycin, and bleomycin. As with the drugs mentioned above, use of these agents to treat particular types of cancers is well known in the art, and they can be used in combination with halichondrin B analog treatment to treat these and other types of cancers. As a specific, non-limiting example, an anthracycline, such as doxorubicin, can be administered in conjunction with halichondrin B therapy for the treatment of breast or pancreatic cancers. Alternatively, a third agent, cyclophosphamide, can be used in this method.

Alkylating agents comprise another class of chemotherapeutic drugs that can be administered in conjunction with a halichondrin B analog, according to the invention. Examples of such drugs include procarbazine, dacarbazine, altretamine, cisplatin, carboplatin, and nitrosoureas. Halichondrin B analogs can be used with these agents in the treatment of cancers that these agents are known in the art to be used to treat, as well as in the treatment of other cancers. For example, a halichondrin B analog can be used in conjunction with carboplatinum in the treatment of non-small cell lung carcinoma or ovarian cancer.

An additional type of chemotherapeutic drug with which halichondrin B analogs can be administered, according to the invention, is plant alkaloids, such as vinblastine, vincristine, etoposide, teniposide, topotecan, irinotecan, paclitaxel, and docetaxel. As specific, non-limiting examples, a halichondrin B analog can be used in conjunction with irinotecan for the treatment of colorectal cancer, or with topotecan in the treatment of ovarian or non-small cell lung cancers.

Further types of anti-cancer agents that can be used in conjunction with halichondrin B analog treatment, according to the invention, are anticoagulants and antithrombotic agents. For example, heparin (e.g., low molecular weight heparin or heparin sulfate) or warfarin can be used. Use of these agents in treating patients by, for example, injection or oral administration, is well known in the art, and thus they can readily be adapted by those of skill in the art for use in the present invention.

Numerous approaches for administering anti-cancer drugs are known in the art, and can readily be adapted for use in this invention. In the case of one or more drugs that are to be administered in conjunction with a halichondrin B analog, for example, the drugs can be administered together, in a single composition, or separately, as part of a comprehensive treatment regimen. For systemic administration, the drugs can be administered by, for example, intravenous infusion (continuous or bolus). Appropriate scheduling and dosing of such administration can readily be determined by those of skill in this art based on, for example, preclinical studies in animals and clinical studies (e.g., phase I studies) in humans. In addition, analysis of treatment using similar drugs, as well as monitoring factors such as blood counts (e.g., neutrophil and platelet counts) and vital signs in patients can be used, as is well understood in the art.

Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug (or a subset of drugs).

As a specific, non-limiting example of a treatment regimen included in the invention, a halichondrin B analog (e.g., 0.01-5 mg/m$^2$) can be administered to a patient by intravenous infusion for 0.5-3 hours, followed by intravenous infusion of another drug (e.g., gemcitabine, e.g., 500-900 mg/m$^2$) for 0.5-3 hours. This course of treatment can be repeated every 2-3 weeks, as determined to be tolerable and effective by those of skill in the art. In a variation of this method, the treatment is carried out with both drugs on the first day, as is noted above, but then is followed up with treatment using only the secondary drug (e.g., gemcitabine) in ensuing weeks.

Further, as is well known in the art, treatment using the methods of the invention can be carried out in conjunction with the administration of antiemetics, which are drugs that are used to reduce the nausea and vomiting that are common side effects of cancer chemotherapy. Examples of such drugs include major tranquilizers (e.g., phenothiazines, such as chlorpromazine and prochlorperazine), dopamine antagonists (e.g., metoclopramide), serotonin antagonists (e.g., ondansetron and granisetron), cannabinoids (e.g., dronabinol), and benzodiazepine sedatives.

In addition to the cancers mentioned above, the methods and compositions of the invention can be used to treat the following types of cancers, as well as others: skin (e.g., squamous cell carcinoma, basal cell carcinoma, or melanoma), prostate, brain and nervous system, head and neck, testicular, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Other types of cancers that can be treated using the methods of the invention include fibrosarcoma, neurectodermal tumor, mesothelioma, epidermoid carcinoma, and Kaposi's sarcoma.

The invention also includes compositions that include a halichondrin B analog in combination with an additional therapeutic agent(s), such as any of those agents listed above. The drugs in these compositions preferably are formulated for administration to patients (e.g., in physiological saline) or, alternatively, can be in a form requiring further processing prior to administration. For example, the compositions can include the drugs in a lyophilized form or in a concentrated form requiring dilution. Formulation of drugs for use in chemotherapeutic methods can be carried out using standard methods in the art (see, e.g., Remington's Pharmaceutical Sciences (18$^{th}$ edition), ed. A. Gennaro, 1990, Mack Publishing Co., Easton, Pa.).

EXAMPLES

Single Crystal X-Ray Diffraction Data Collection and Structure Determinations

Data were collected using a Bruker SMART APEX CCD (charge coupled device) based diffractometer equipped with an Oxford Cryostream low-temperature apparatus operating at 193 K. Data were measured using omega scans of 0.3° per frame for 30 seconds, such that a hemisphere was collected. A total of 1271 frames were collected with a maximum resolution of 0.76 Å. The first 50 frames were recollected at the end of data collection to monitor for decay. Cell parameters were retrieved using SMART software (SMART V 5.625 (NT) Software for the CCD Detector System; Bruker Analytical X-ray Systems, Madison, Wis. (2001)). and refined using SAINT on all observed reflections. Data reduction was performed using the SAINT software (SAINT V 6.22 (NT) Software for the CCD Detector System Bruker Analytical X-ray Systems, Madison, Wis. (2001). which corrects for Lp and decay. The structures were solved by the direct method using the SHELXS-97 program (Sheldrick, G. M. SHELXS-90, Program for the Solution of Crystal Structure, University of Göttingen, Germany, 1990.) and refined by least squares method on F$^2$, SHELXL-97, (Sheldrick, G. M. SHELXL-97, Program for the Refinement of Crystal Structure, University of Göttingen, Germany, 1997.) incorporated in SHELXTL-PC V 6.10, (SHELXTL 6.1 (PC-Version), Program library for Structure Solution and Molecular Graphics; Bruker Analytical X-ray Systems, Madison, Wis. (2000)).

X-Ray Powder Diffraction (XRPD) Data Collection Procedure

A small amount of crystalline material was used for the XRPD diffraction studies described below. The material was not crushed, and so may have preferred orientation effects. Using a quartz plate, on the Scintag Diffractometer. Data was acquired under normal powder diffraction condition, with 2-theta range of 5-70 degrees, using copper radiation. No background correction was applied. Table 1 lists the data acquisition parameters.

TABLE 1

| XRPD Measurement Conditions | |
|---|---|
| X-ray diffractometer: | Scintag |
| Target: | Cu |
| Detector: | Lithium Drifted Diode |
| Tube voltage: | 40 kV |
| Tube current: | 30 mA |
| Slit: | DS 1.0, RS 0.3 mm, SS 2 mm tube, 0.5 mm detector |
| Scan speed: | 1°/min |
| Step/Sampling: | 0.02° |
| Scan range: | 5 to 70° |
| Sample holder: | Quartz holder (25 mm × 25 mm) |
| Goniometer: | Theta-Theta, fixed horizontal mount, goniometer |
| Filter: | Electronic |
| Monochromator: | not used |

Example 1

Characterization of Crystalline ER-076349 Monohydrate

XRPD patterns of ethanol, isopropanol (IPA), propionitrile are identical to acetonitrile/water sample. Characterization as monohydrate was based on this comparison. X-ray unit cell of acetonitrile/water crystal clearly showed the presence of single water molecule.

A. Crystallization Procedures for ER-076349 Monohydrate

Crystallization of ER-076349 from ethanol, isopropanol, and propionitrile (XRPD sample): ER-076349 was dissolved in solvent (5 vol). The solution was allowed to evaporate at room temperature and a crystal suitable for XRPD testing formed over 16 to 24 hr.

Crystallization of ER-076349 from acetonitrile/water solution (XRPD sample): ER-076349 was dissolved in acetonitrile (1 vol). To this solution was slowly added a water/acetonitrile solution (10 vol, 2 parts water, 1 part acetonitrile); if the solution becomes cloudy, a minimal amount of acetonitrile can be added. The solution was seeded with ER-076349 (0.004 wts). The mixture is stirred at room temperature and the solvent evaporated under inert gas flow until the acetonitrile level is ≤5%. The solids were slurried in water (5 vol) and the mixture was filtered. The filtered solids were dried under high vacuum and inert gas flow for 12 to 24 hours.

Crystallization of ER-076349 from acetonitrile/water solution (single crystal): ER-076349 was dissolved in acetonitrile (5 vol). Water (0.5 vol) was then added. The container was stored at room temperature and vented for slow evaporation of solvent for 4 weeks, and the single crystal suitable for X-ray structure study formed slowly.

B. Single Crystal X-Ray Determination of ER-076349 Monohydrate

A colorless plate crystal with dimensions 0.10×0.10×0.04 mm was mounted on a 0.2 nm nylon loop using very small amount of paratone oil. The single crystal structure, shown in FIG. 1-A, was determined using the procedure described above. Table 2 lists the crystal data and structure refinement parameters used to determine the single crystal structure of ER-076349 monohydrate. The structure was solved in the space group $P2_12_12_1$ (#19) by analysis of systematic absences. All non-hydrogen atoms were refined anisotropically. Hydrogens were calculated by geometrical methods and refined as a riding model. The crystal used for the diffraction study showed no decomposition during data collection. All drawings were done at 50% ellipsoids. FIG. 1-B is the crystal packing diagram of ER-076349 monohydrate along the b-axis, which shows the best diagram of the hydrogen bonding within the crystal, dotted lines.

TABLE 2

Crystal data and structure refinement for ER-076349 Monohydrate.

| | |
|---|---|
| Empirical formula | $C_{40}H_{59}O_{13}$ |
| Formula weight | 747.87 |
| Temperature | 193(2) K |
| Wavelength | 0.71073 Å |
| Crystal system | Orthorhombic |
| Space group | P2(1)2(1)2(1) |
| Unit cell dimensions | a = 9.9189(14) Å    α = 90°. |
| | b = 11.3394(17) Å   β = 90°. |
| | c = 34.029(5) Å     γ = 90°. |
| Volume | 3827.3(10) Å$^3$ |
| Z | 4 |
| Density (calculated) | 1.298 Mg/m$^3$ |
| Absorption coefficient | 0.096 mm$^{-1}$ |
| F(000) | 1612 |
| Crystal size | 0.10 × 0.10 × 0.04 mm$^3$ |
| Theta range for data collection | 1.20 to 26.39°. |
| Index ranges | −10 <= h <= 12, −13 <= k <= 14, −32 <= l <= 42 |
| Reflections collected | 23198 |
| Independent reflections | 7808 [R(int) = 0.1131] |
| Completeness to theta = 26.39° | 99.9% |
| Absorption correction | None |
| Refinement method | Full-matrix least-squares on F$^2$ |
| Data/restraints/parameters | 7808/0/482 |
| Goodness-of-fit on F$^2$ | 0.938 |
| Final R indices [I > 2sigma(I)] | R1 = 0.0627, wR2 = 0.0911 |
| R indices (all data) | R1 = 0.1693, wR2 = 0.1150 |
| Absolute structure parameter | −0.7(12) |
| Largest diff. peak and hole | 0.380 and −0.182 e.Å$^{-3}$ |

C. X-Ray Powder Diffraction (XRPD) Characterization of ER-076349 Monohydrate

FIG. 1-C is the XRPD pattern of ER-076340 monohydrate crystallized from isopropyl alcohol as described above. Table 3 shows the list of peaks with relative intensities in the XRPD pattern.

TABLE 3

XRPD Peaks of ER-076349 monohydrate

| Position (2θ) | Rel. Int. (%) |
|---|---|
| 18.2 | 100.0% |
| 20.8 | 91.0% |
| 18.7 | 60.3% |
| 20.3 | 59.6% |
| 10.4 | 59.3% |
| 22.2 | 51.2% |
| 15.9 | 42.5% |
| 13.0 | 37.4% |
| 9.3 | 37.1% |
| 14.2 | 35.5% |
| 12.1 | 29.3% |
| 11.9 | 28.3% |
| 5.2 | 22.9% |

FIG. 1-D is a stacked plot of representative XRPD patterns of ER-076349 monohydrate acquired from various recrystallization solvents, including acetonitrile and water, ethanol, isopropanol, and propionitrile. The same method of pattern acquisition as described above was used.

FIGS. 1-E, 1-F, and 1-G depict differential scanning calorimetry (DSC) thermograms of ER-076349 monohydrate. FIG. 1-E depicts a plot of the DSC of ER-076349 crystallized from ethanol solution. The DSC shows an endothermic peak at 160° C. FIG. 1-F depicts a plot of the DSC of ER-076349 crystallized from isopropanol solution. The DSC shows an endothermic peak at 157° C. FIG. 1-G depicts a plot of the DSC of ER-076349 crystallized from propionitrile solution. The DSC shows an endothermic peak at 161° C.

Example 2

Characterization of ER-818906 (Epi-C20 Diol), a Mono-Acetonitrile Solvate

A. Crystallization Procedure for Generation of X-Ray and XRPD Crystal Samples

ER-818906 (1 wt) was suspended in acetonitrile (10 vol) and warmed gently to ensure complete dissolution. The solution was held at room temperature and crystal growth initiated after 30 minutes. The single crystal sample suitable for X-ray structure analysis formed after 16 to 24 hours. The chemical structure of ER-818906 (epi-C20 diol) is shown below.

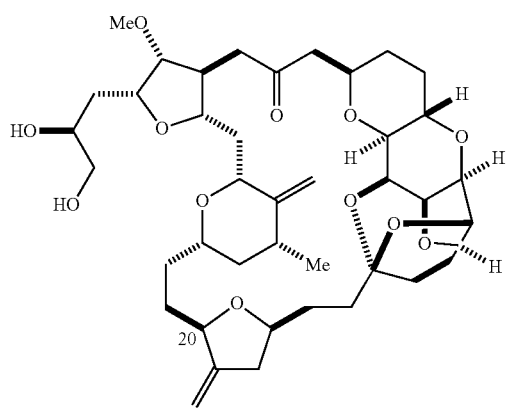

ER-818906
(Epi-C20 Diastereomer)

Figure 2A:
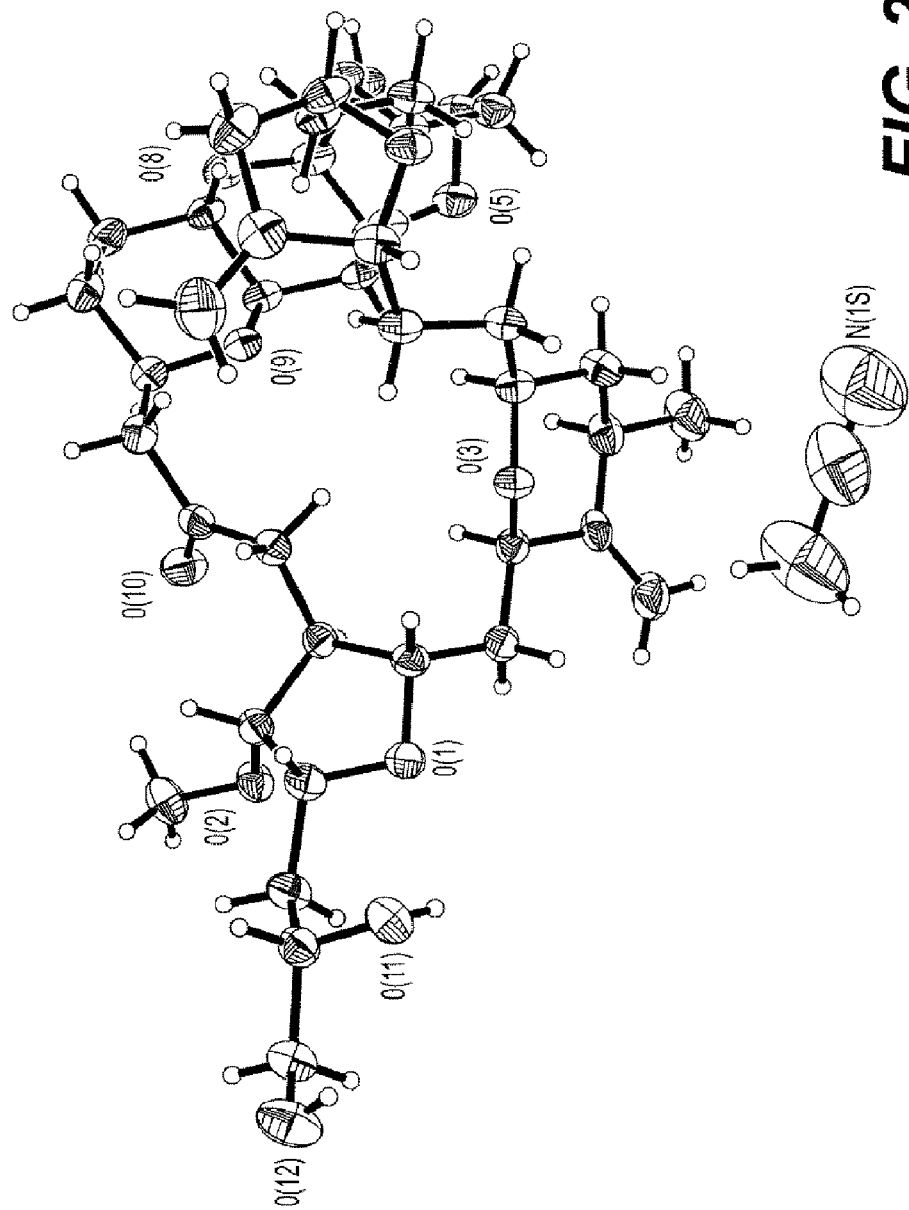
FIG. 2-A is an ORTEP drawing of the single crystal structure of ER-818906 mono-acetonitrile solvate.
Figure 2B:
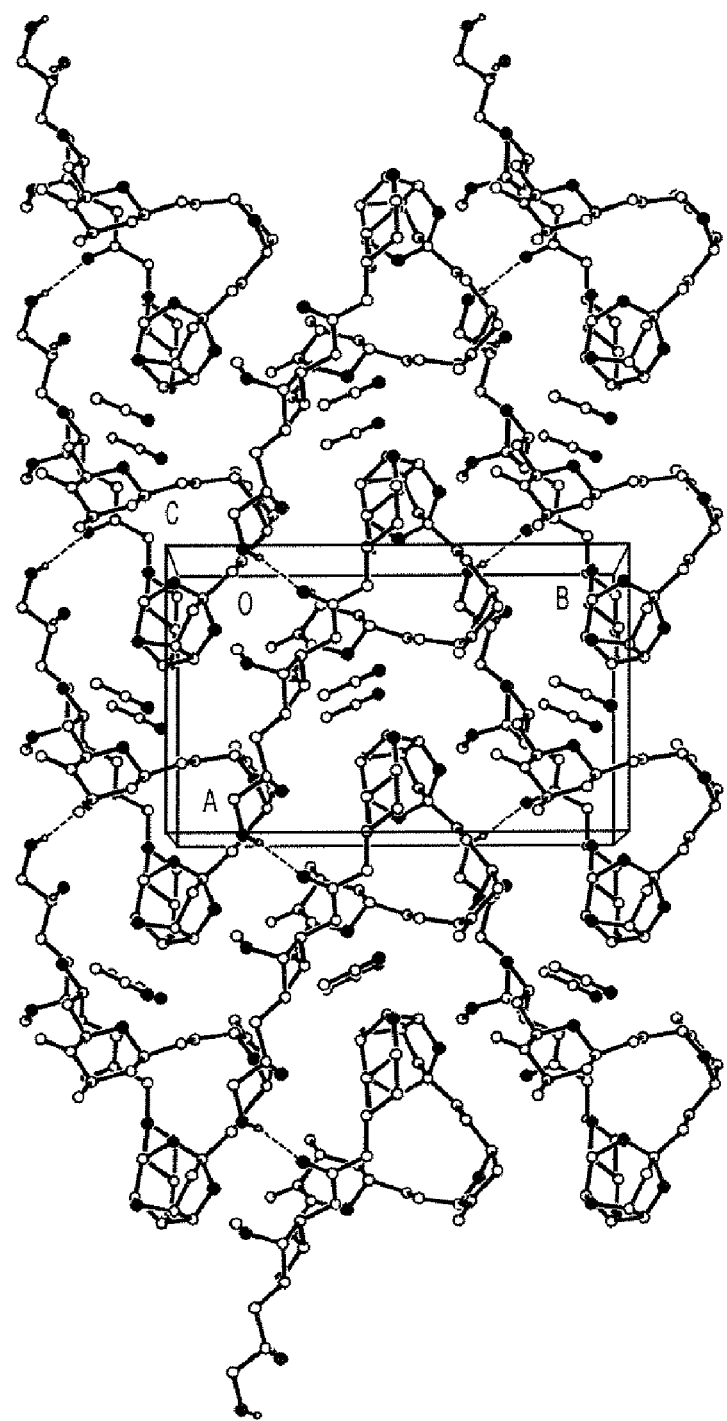
Figure 2C:
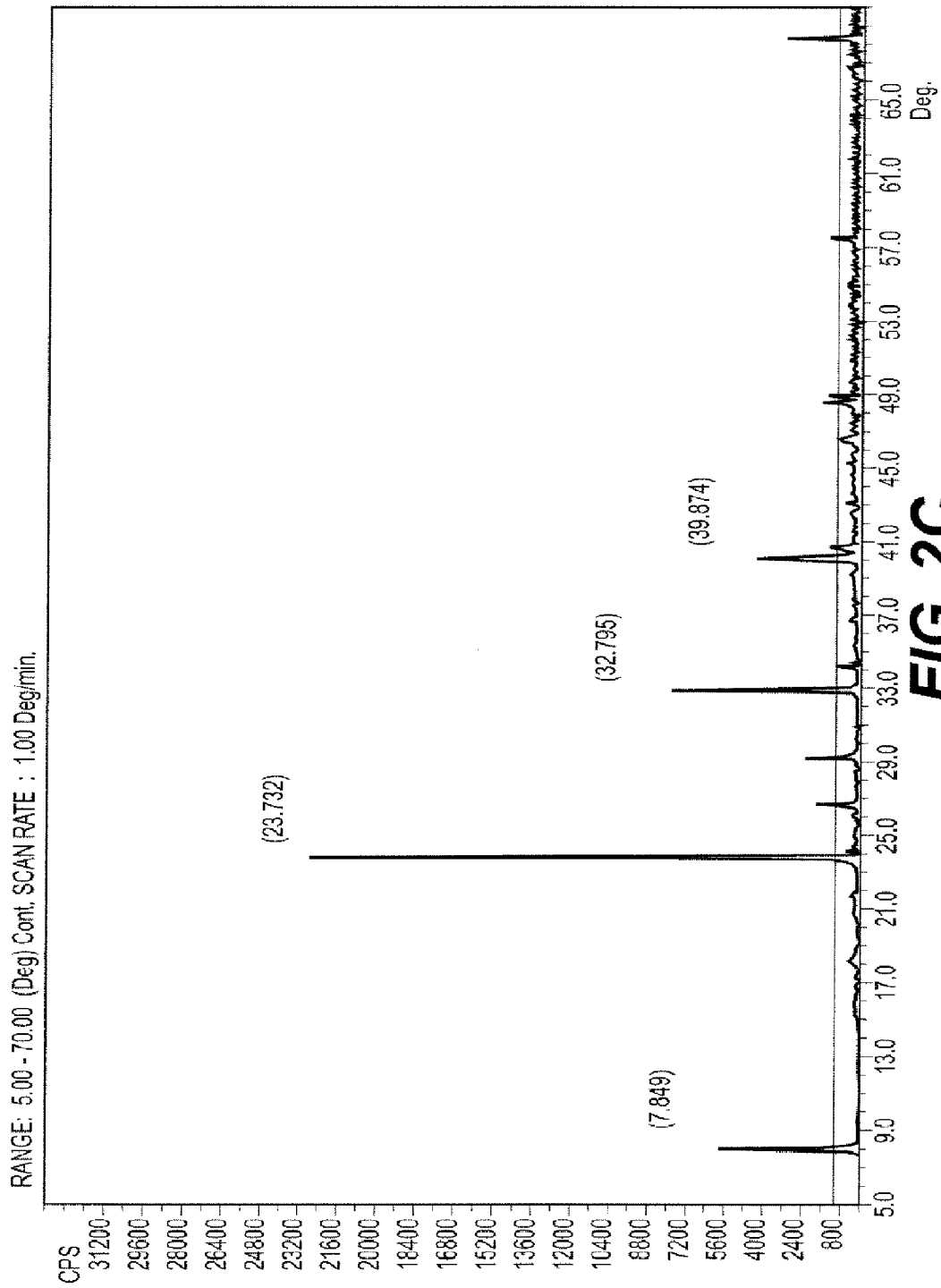

B. Single Crystal X-Ray Determination of ER-818906 (Epi-C20 Diol) Mono-Acetonitrile Solvate A colorless block crystal with dimensions 0.12×0.12×0.10 mm was mounted on a 0.2 nm nylon loop using very small amount of paratone oil. The single crystal structure, shown in FIG. 2-A, was determined using the procedure described above. Table 3 lists the crystal data and structure refinement parameters used to determine the single crystal structure of ER-818906 mono-acetonitrile solvate. The structure was solved in the space group $P2_1$ (#4) All non-hydrogen atoms were refined anisotropically. Hydrogens were calculated by geometrical methods and refined as a riding model. The Flack parameter was used to analyze the crystal. If the Flack parameter value is near zero, the absolute structure given by the structure element refinement is likely correct; if the value is near 1.0, then the inverted structure (the other enantiomer) is likely correct; if the value is near 0.5, the crystal is likely racemic. See Flack, H. D. *Acta Cryst. A*39, 1983, 876-881. The Flack parameter was refined to 0.3(4). The chirality of this compound was confirmed by its synthetic source. The crystal used for the diffraction study showed no decomposition during data collection. All drawing are done at 50% ellipsoids. FIG. 2-B is the crystal packing diagram of ER-818906 monoacetonitrile solvate along the c-axis.

TABLE 3

Crystal data and structure refinement for ER-818906 Mono-Acetonitrile Solvate.

| | |
|---|---|
| Empirical formula | $C_{42}H_{61}NO_{12}$ |
| Formula weight | 771.92 |
| Temperature | 193(2) K |
| Wavelength | 0.71073 Å |
| Crystal system | Monoclinic |
| Space group | P2(1) |
| Unit cell dimensions | a = 10.610(4) Å    α = 90°. |
| | b = 17.114(7) Å    β = 94.341(7)°. |
| | c = 11.251(5) Å    γ = 90°. |
| Volume | 2036.9(15) Å$^3$ |
| Z | 2 |
| Density (calculated) | 1.259 Mg/m$^3$ |
| Absorption coefficient | 0.091 mm$^{-1}$ |
| F(000) | 832 |
| Crystal size | 0.12 × 0.12 × 0.10 mm$^3$ |
| Theta range for data collection | 1.82 to 27.87°. |
| Index ranges | −13 <= h <= 12, −22 <= k <= 22, −14 <= l <= 14 |
| Reflections collected | 14960 |
| Independent reflections | 9147 [R(int) = 0.0160] |
| Completeness to theta = 27.87° | 98.6% |
| Absorption correction | EMPIRICAL |
| Max. and min. transmission | 0.9909 and 0.9891 |
| Refinement method | Full-matrix least-squares on F$^2$ |
| Data/restraints/parameters | 9147/1/501 |
| Goodness-of-fit on F$^2$ | 1.044 |
| Final R indices [I > 2sigma(I)] | R1 = 0.0410, wR2 = 0.0881 |
| R indices (all data) | R1 = 0.0473, wR2 = 0.0909 |
| Absolute structure parameter | 0.3(6) |
| Largest diff. peak and hole | 0.222 and −0.199 e.Å$^{-3}$ |

C. X-Ray Powder Diffraction (XRPD) Characterization of ER-818906 (Epi-C20 Diol) Mono-Acetonitrile Solvate A small amount of material was left after removing a sample for single crystal study in Example 2A. The XRPD pattern was obtained as described above. The XRPD pattern is shown in FIG. 2-C. Table 4 shows the list of peaks with relative intensities in the XRPD pattern.

TABLE 4

XRPD Peaks of ER-818906 (epi-C20 diol)

| Position (2θ) | Rel. Int. (%) |
|---|---|
| 23.7 | 100.0 |
| 32.8 | 35.6 |
| 7.9 | 25.0 |
| 40.0 | 19.4 |
| 68.4 | 14.5 |
| 23.9 | 12.2 |
| 29.2 | 10.4 |
| 26.7 | 7.7 |
| 8.1 | 7.3 |
| 48.6 | 7.2 |
| 57.5 | 6.4 |
| 48.9 | 5.9 |
| 40.7 | 5.7 |
| 34.1 | 4.0 |

Example 3

Characterization of ER-819531 (Epi-C23 Diol) Monohydrate

A. Crystallization Procedure for XRPD Quality Sample

ER-819531 (1 wt) was dissolved in acetonitrile (10 vol) at room temperature and the temperature was decreased to −20° C. and held at this temperature for 16 hours. Clusters of crystal suitable for powder XRPD test formed after 16 hours. The chemical structure of ER-819531 (epi-C23 diol) is shown below.

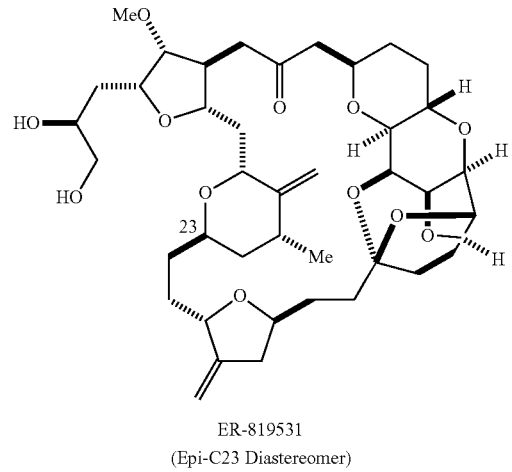

ER-819531
(Epi-C23 Diastereomer)

B. Single Crystal X-Ray Determination of ER-819531 (Epi-C23 Diol) Monohydrate

Figure 3A:
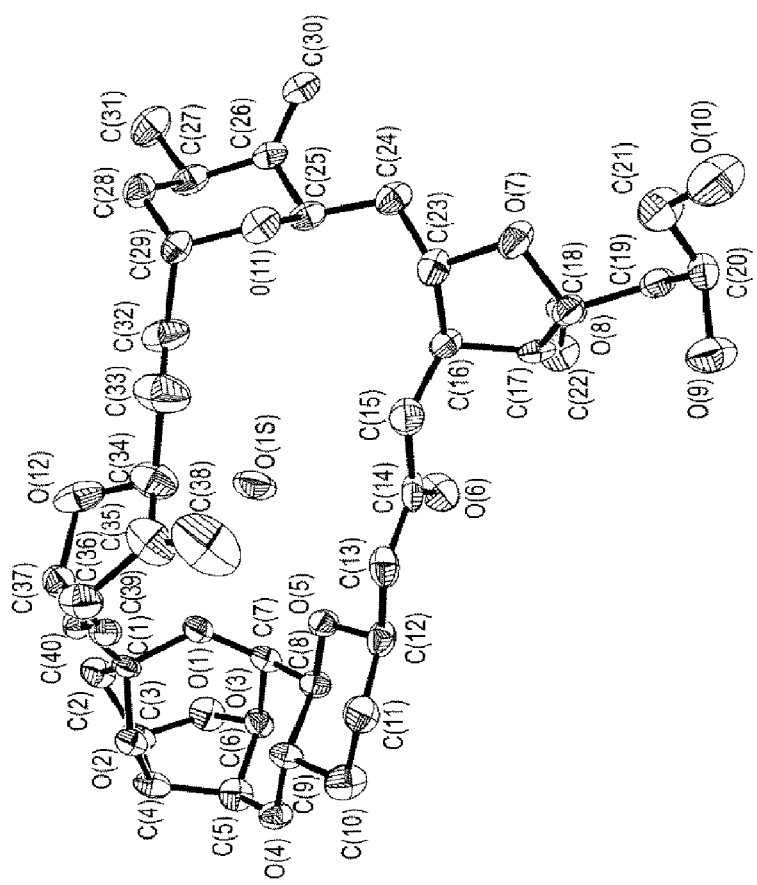
FIG. 3-A is an ORTEP drawing of the single crystal structure of ER-819531 (epi-C23 diol) monohydrate.
Figure 3B:
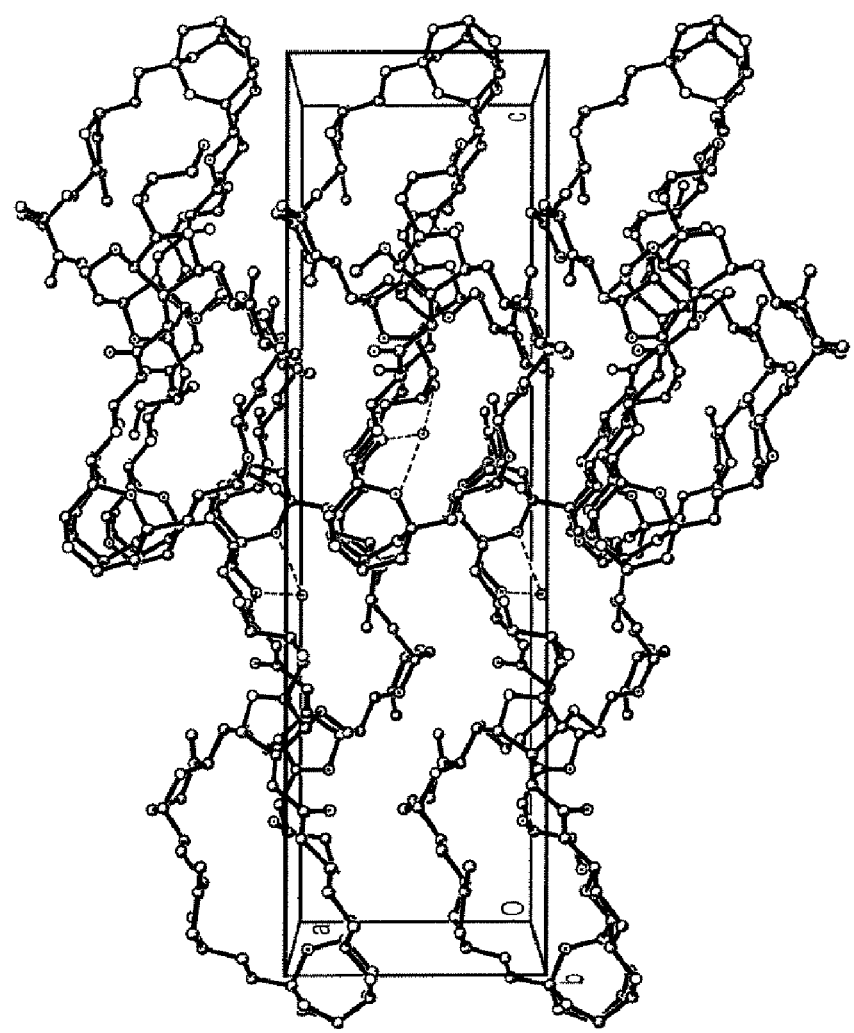
Figure 3C:
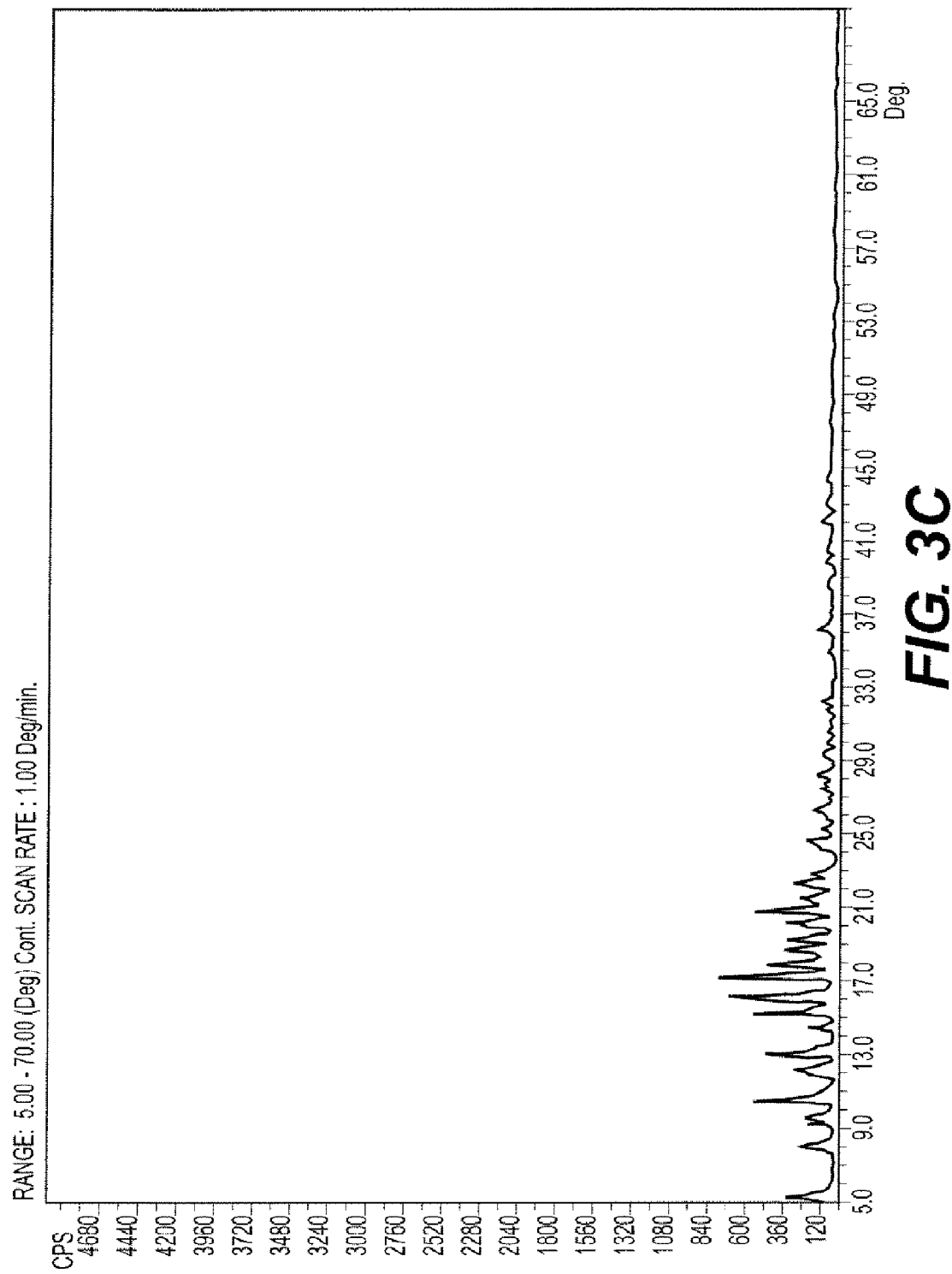

A portion of sample ER-819531 was dissolved in a mixture of acetonitrile, several drops of toluene, and one drop of water. This was then allowed to slowly evaporate in a small vial. This resulted in single crystals, one of which was chosen to be used in this study. A colorless block crystal with dimensions 0.12×0.12×0.04 mm was mounted on a 0.2 nm nylon loop using very small amount of paratone oil. The single crystal structure, shown in FIG. 3-A, was determined using the procedure described above. Table 5 lists the crystal data and structure refinement parameters used to determine the single crystal structure of ER-819531 monohydrate. The structure was solved in the space group $P2_12_12_1$ (#19) by analysis of systematic absences. All non-hydrogen atoms are refined anisotropically. Hydrogens were calculated by geometrical methods and refined as a riding model. The Flack parameter was used to analyze the crystal. If the Flack parameter value is near zero, the absolute structure given by the structure element refinement is likely correct; if the value is near 1.0, then the inverted structure (the other enantiomer) is likely correct; if the value is near 0.5, the crystal is likely racemic. See Flack, H. D. *Acta Cryst*. *A*39, 1983, 876-881. The Flack parameter was refined to 0.50(16). The chirality of this compound was confirmed by its synthetic source. The crystal used for the diffraction study showed no decomposition during data collection. All drawing are done at 50% ellipsoids. FIG. 3-B is the crystal packing diagram along the b-axis which shows the hydrogen bonding within the crystal, dotted lines

TABLE 5

Crystal data and structure refinement for ER-819531 monohydrate

| | |
|---|---|
| Empirical formula | $C_{40}H_{60}O_{13}$ |
| Formula weight | 748.88 |
| Temperature | 193(2) K |
| Wavelength | 0.71073 Å |
| Crystal system | Orthorhombic |
| Space group | P2(1)2(1)2(1) |
| Unit cell dimensions | a = 9.6545(16) Å  α = 90°. |
| | b = 11.6562(19) Å  β = 90°. |
| | c = 33.618(6) Å  γ = 90°. |
| Volume | 3783.1(11) Å$^3$ |
| Z | 4 |
| Density (calculated) | 1.315 Mg/m$^3$ |
| Absorption coefficient | 0.097 mm$^{-1}$ |
| F(000) | 1616 |
| Crystal size | 0.12 × 0.12 × 0.04 mm$^3$ |
| Theta range for data collection | 1.85 to 23.25°. |
| Index ranges | −10 <= h <=10, −12 <= k <= 12, −37 <= l <= 25 |
| Reflections collected | 18298 |
| Independent reflections | 5420 [R(int) = 0.0866] |
| Completeness to theta = 23.25° | 100.0% |
| Absorption correction | None |
| Refinement method | Full-matrix least-squares on F$^2$ |
| Data/restraints/parameters | 5420/0/482 |
| Goodness-of-fit on F$^2$ | 1.025 |
| Final R indices [I > 2sigma(I)] | R1 = 0.0670, wR2 = 0.1275 |
| R indices (all data) | R1 = 0.1032, wR2 = 0.1421 |
| Absolute structure parameter | 0.5(16) |
| Largest diff. peak and hole | 0.503 and −0.261 e.Å$^{-3}$ |

C. X-Ray Powder Diffraction (XRPD) Characterization of ER-819531 (Epi-C23 Diol) Monohydrate The XRPD of ER-819531 monohydrate was obtained as described above. The XRPD pattern is shown in FIG. 3-C. Table 6 shows the list of peaks with relative intensities in the XRPD pattern.

TABLE 6

XRPD Peaks of ER-819531 (epi-C23 diol)

| Position (2θ) | Rel. Int. (%) |
|---|---|
| 20.6 | 100.0% |
| 17.2 | 91.9% |
| 16.1 | 83.1% |
| 24.4 | 77.9% |
| 17.8 | 77.8% |
| 22.1 | 76.4% |
| 20.0 | 73.2% |
| 15.2 | 71.9% |
| 19.1 | 71.5% |
| 32.1 | 70.8% |
| 17.3 | 69.4% |
| 18.6 | 69.4% |

TABLE 6-continued

XRPD Peaks of ER-819531 (epi-C23 diol)

| Position (2θ) | Rel. Int. (%) |
|---|---|
| 21.4 | 68.6% |
| 28.2 | 67.5% |
| 26.2 | 67.3% |
| 22.7 | 62.6% |
| 29.2 | 61.8% |
| 13.1 | 55.8% |
| 10.5 | 50.2% |
| 12.3 | 41.6% |
| 14.4 | 40.7% |
| 9.6 | 27.8% |
| 8.1 | 25.5% |

Example 4

Characterization of ER-820057 (epi-C23 amine)

A. Preparation of ER-820057 Crystal Sample

ER-820057 is dissolved in acetonitrile (10 vol) at room temperature and the solution is held at room temperature. Crystal growth is observed after 2 hours. Crystal sample suitable for powder XRPD test was isolated after 16 to 24 hours. The chemical structure of ER-820057 (epi-C23 amine) is shown below.

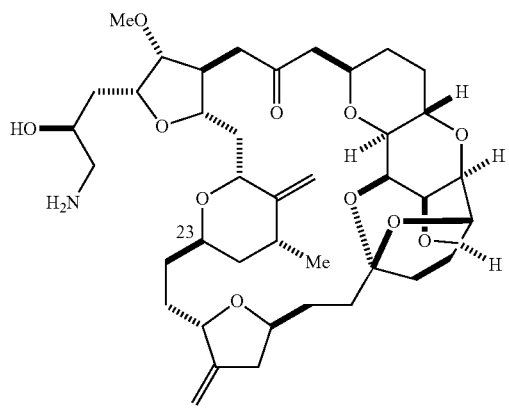

ER-820057
(Epi-C23 Diastereomer)

B. X-Ray Powder Diffraction (XRPD) Characterization of ER-820057 (Epi-C23 Amine)

Figure 4A:
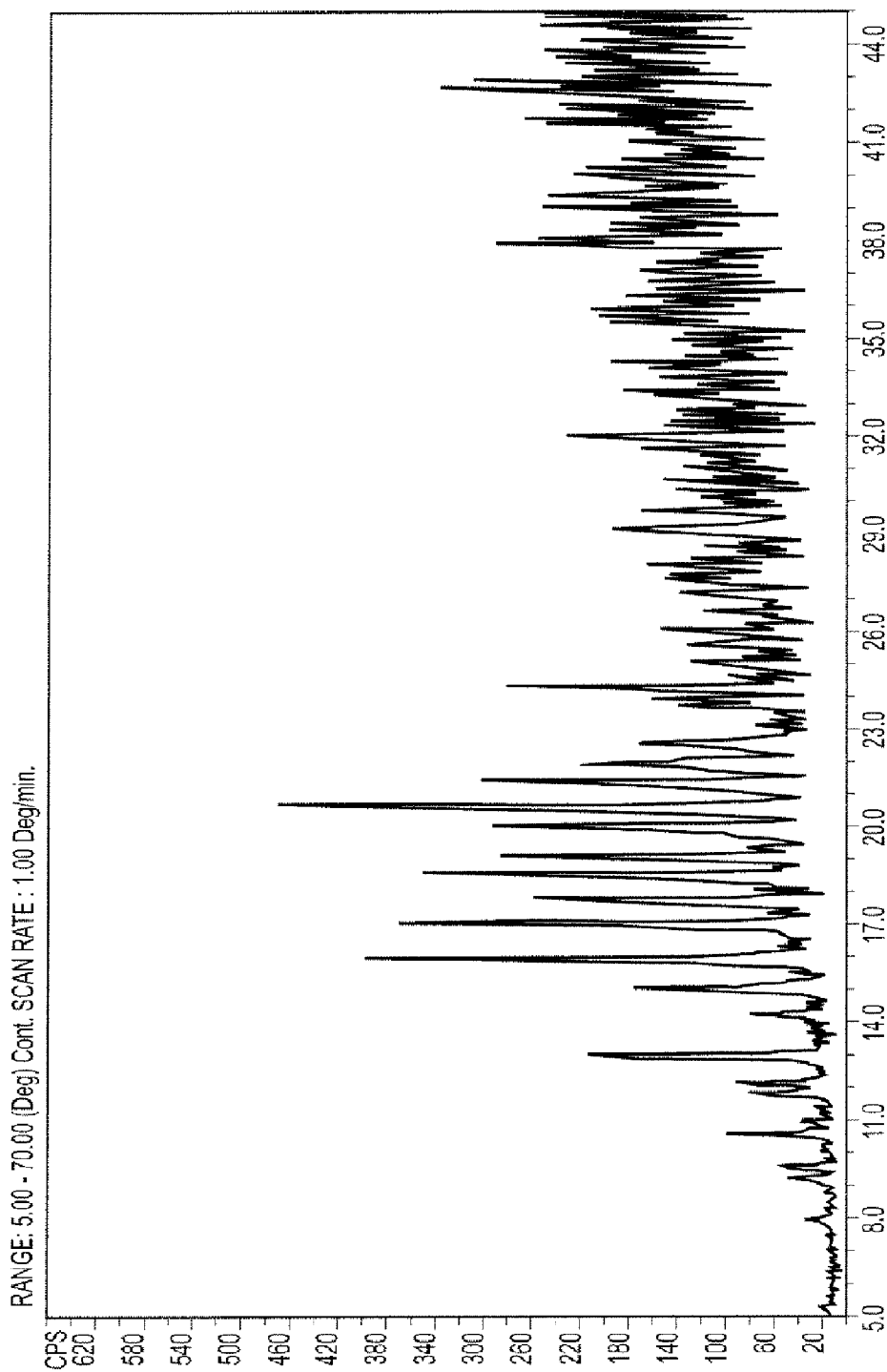
FIG. 4-A is the XRPD pattern of ER-820057 (epi-C23 amine).

The XRPD of ER-820057 was obtained as described above. The XRPD pattern is shown in FIG. 4-A. Table 7 shows the list of peaks with relative intensities in the XRPD pattern.

TABLE 7

XRPD Peaks of ER-820057 (epi-C23 amine)

| Position (2θ) | Rel. Int. (%) |
|---|---|
| 20.6 | 108.9% |
| 15.9 | 100.0% |
| 17.0 | 96.4% |
| 18.5 | 93.9% |
| 21.4 | 87.3% |
| 20.0 | 85.8% |
| 19.1 | 84.6% |

TABLE 7-continued

XRPD Peaks of ER-820057 (epi-C23 amine)

| Position (2θ) | Rel. Int. (%) |
|---|---|
| 24.4 | 84.3% |
| 17.8 | 80.6% |
| 21.9 | 74.8% |
| 13.0 | 73.1% |
| 15.0 | 66.1% |
| 22.6 | 65.4% |
| 24.0 | 63.3% |
| 26.2 | 62.0% |
| 27.3 | 60.1% |
| 25.7 | 56.7% |
| 25.1 | 55.2% |
| 26.8 | 55.2% |
| 10.6 | 50.3% |
| 12.1 | 48.6% |
| 11.9 | 45.2% |
| 14.3 | 44.8% |
| 9.6 | 36.0% |
| 9.2 | 35.1% |
| 10.9 | 31.3% |
| 8.0 | 29.6% |

Example 5

Characterization of ER-111197 (Epi-C34 Diol) Monohydrate

A. Crystallization Procedure for the Generation of X-Ray Quality Crystal

ER-111197 (1 wt) was dissolved in acetonitrile (8 vol). Water (0.8 vol) was added. The solution was left to evaporate at room temperature over 2-3 days. If the crystal does not form, the solution is evaporated to dryness and the procedure is repeated until the crystal forms. The chemical structure of ER-111197 (epi-C34 diol) is shown below.

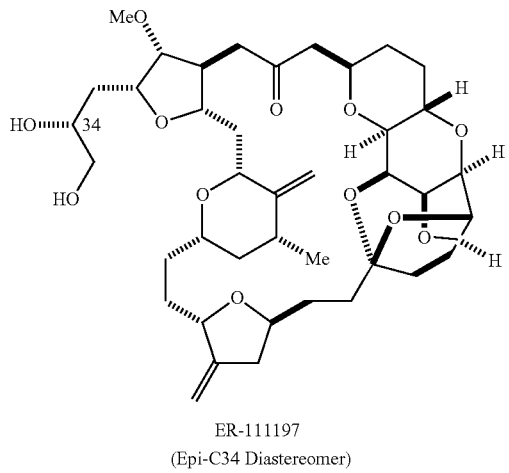

ER-111197
(Epi-C34 Diastereomer)

B. Single Crystal X-Ray Determination of ER-111197 (Epi-C34 Diol) Monohydrate

Figure 5A:
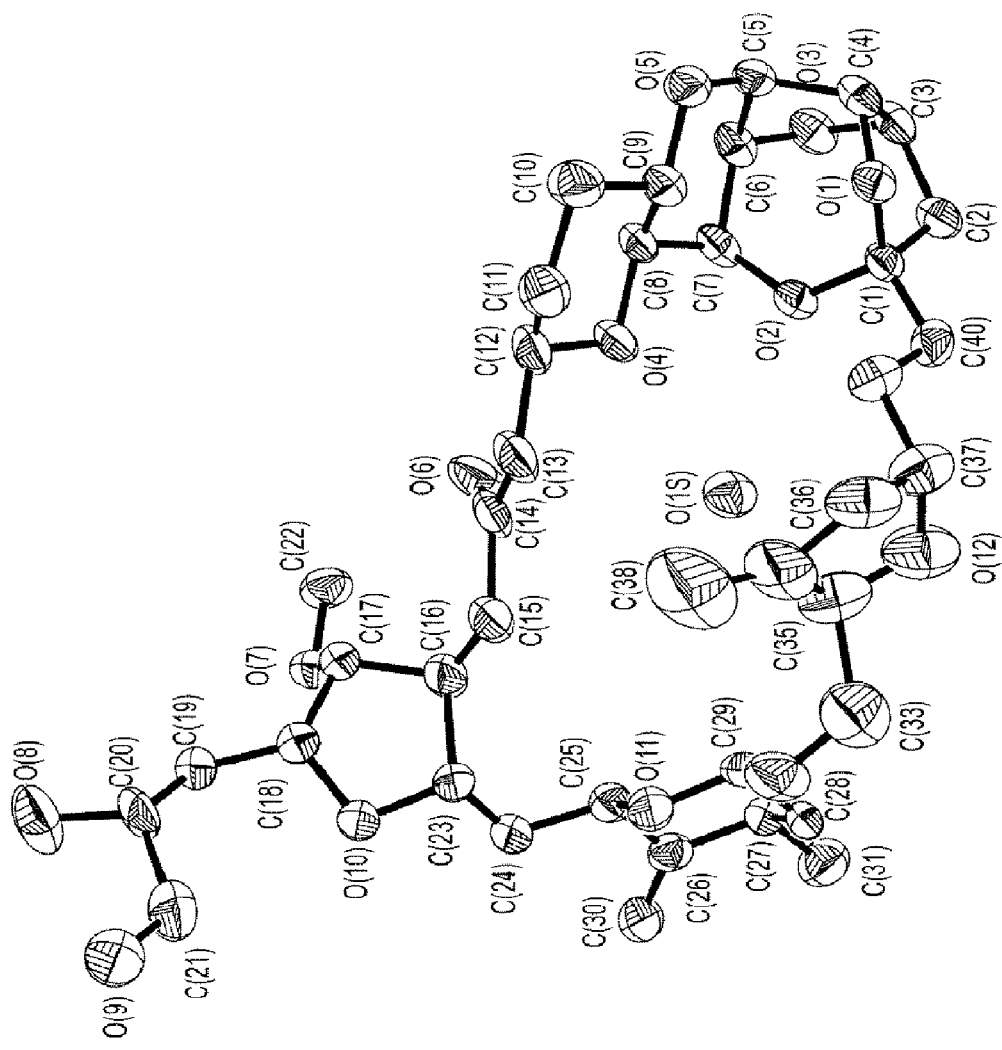
FIG. 5-A is an ORTEP drawing of the single crystal structure of ER-111197 (epi-C34 diol) monohydrate.
Figure 5B:
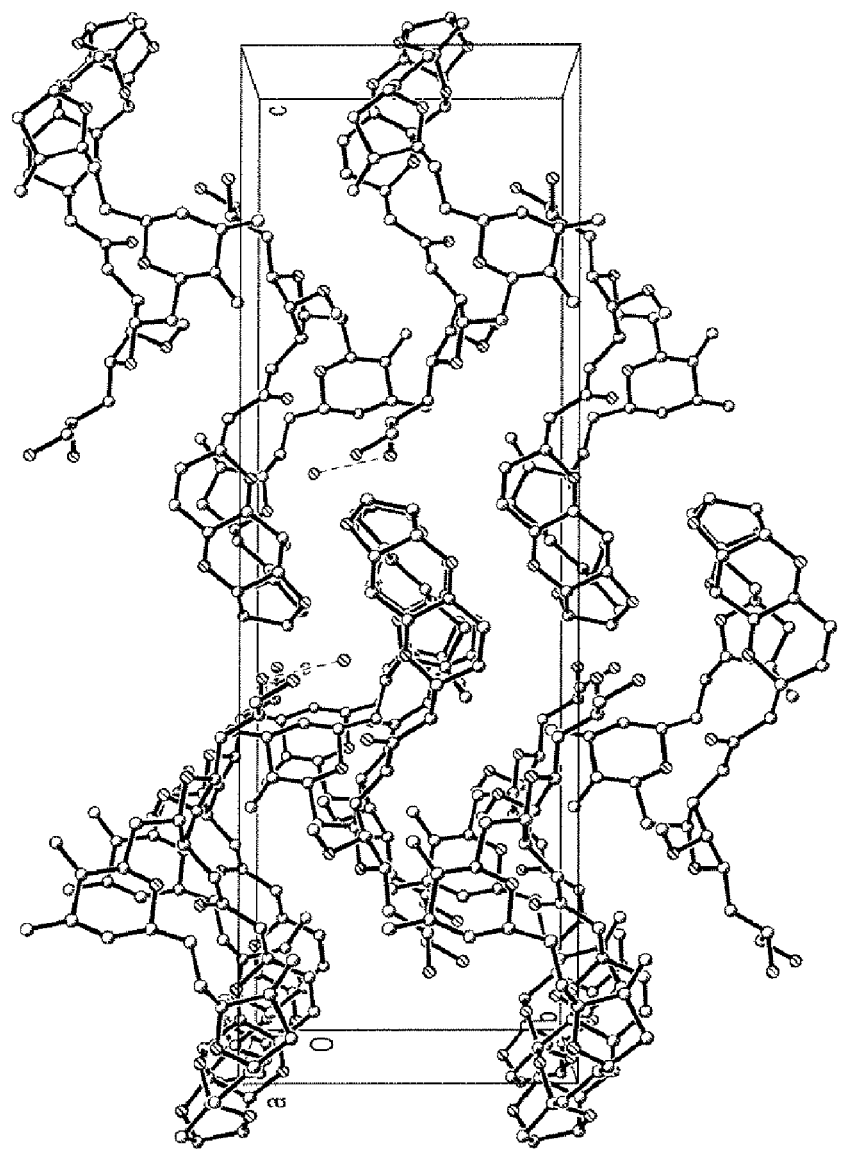
Figure 5C:
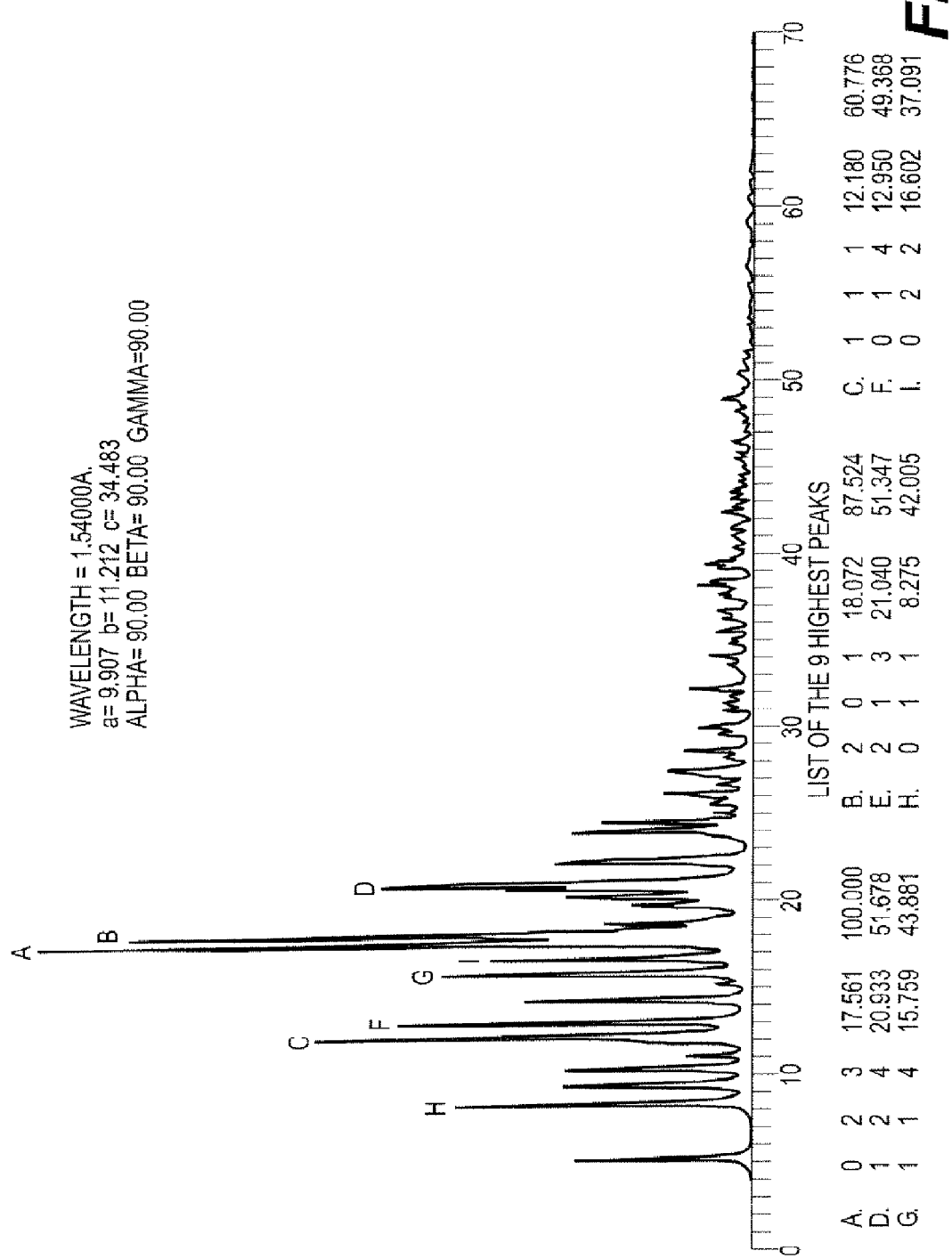
Figure 6A:
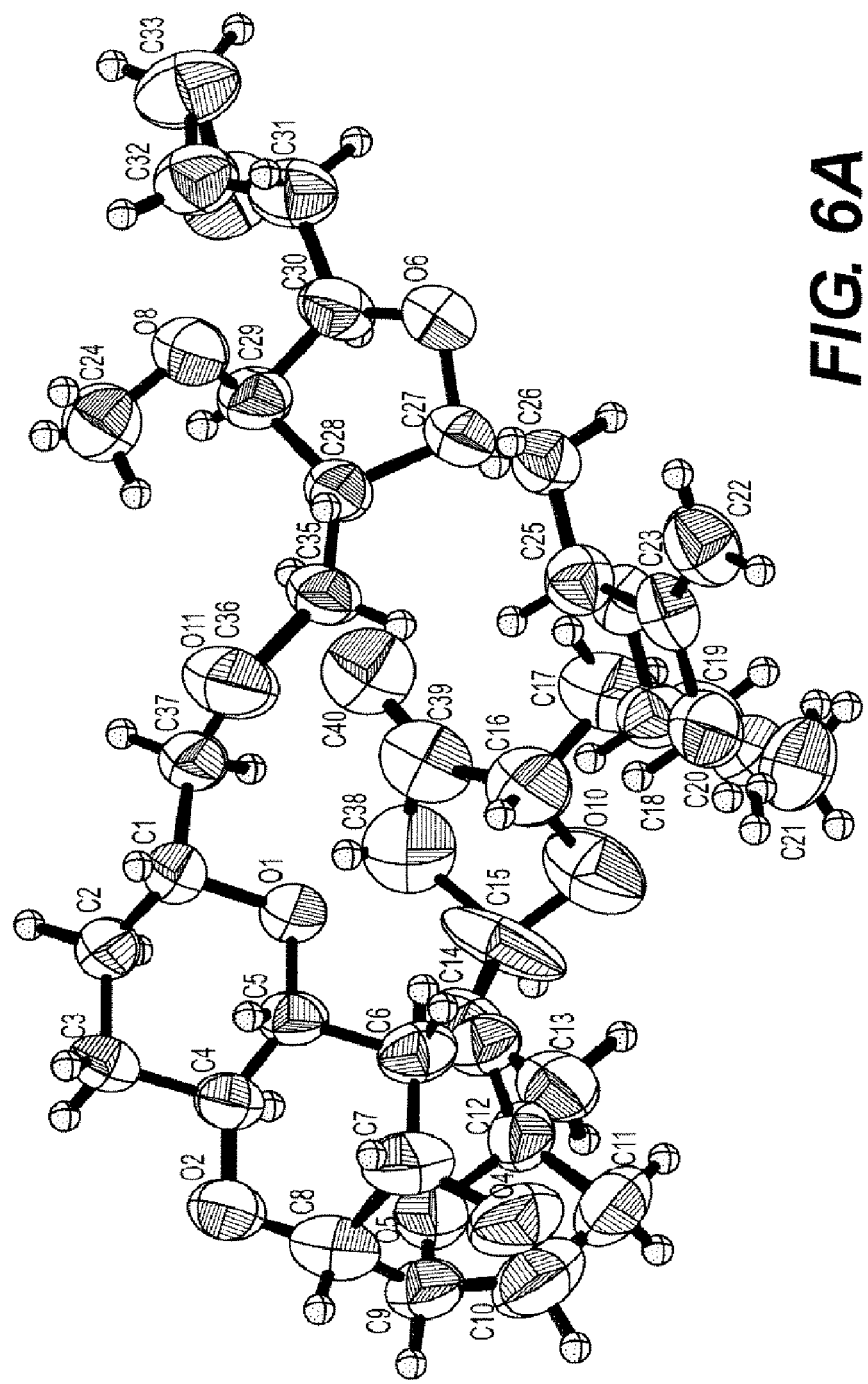
FIG. 6-A is an ORTEP drawing of the single crystal structure of ER-809681 (epoxide).
Figure 6B:
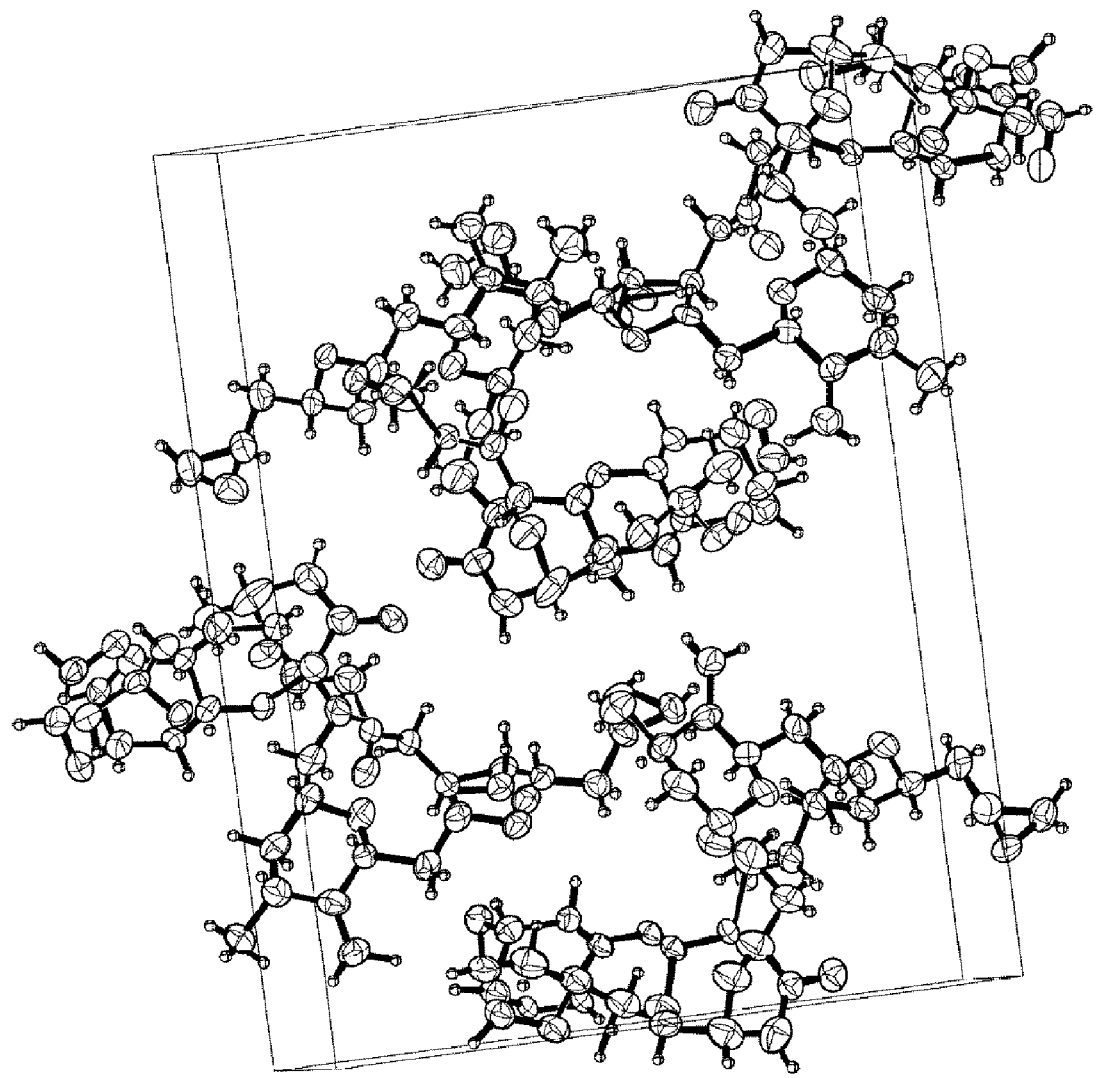
Figure 6C:
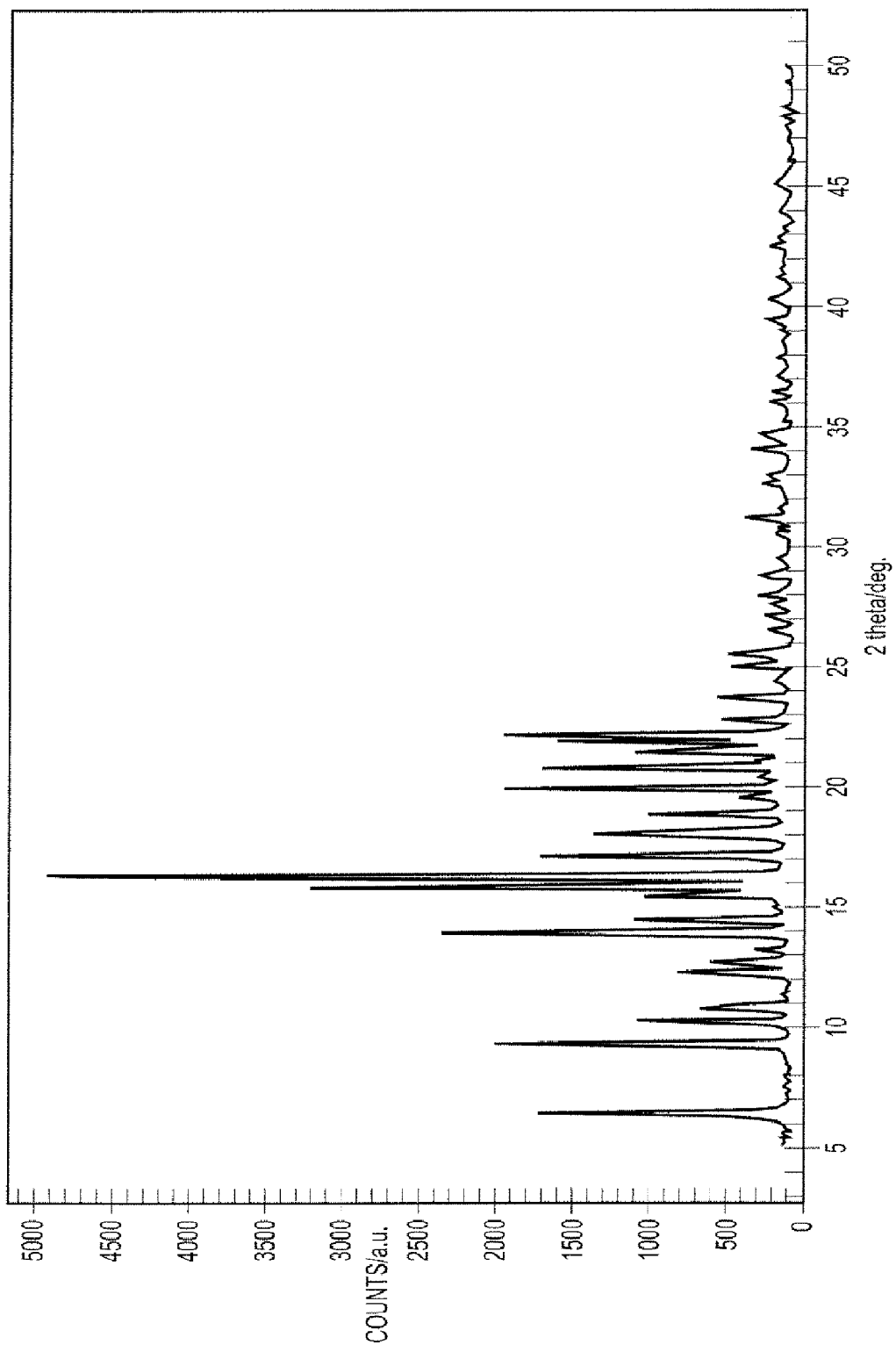
Figure 6D:
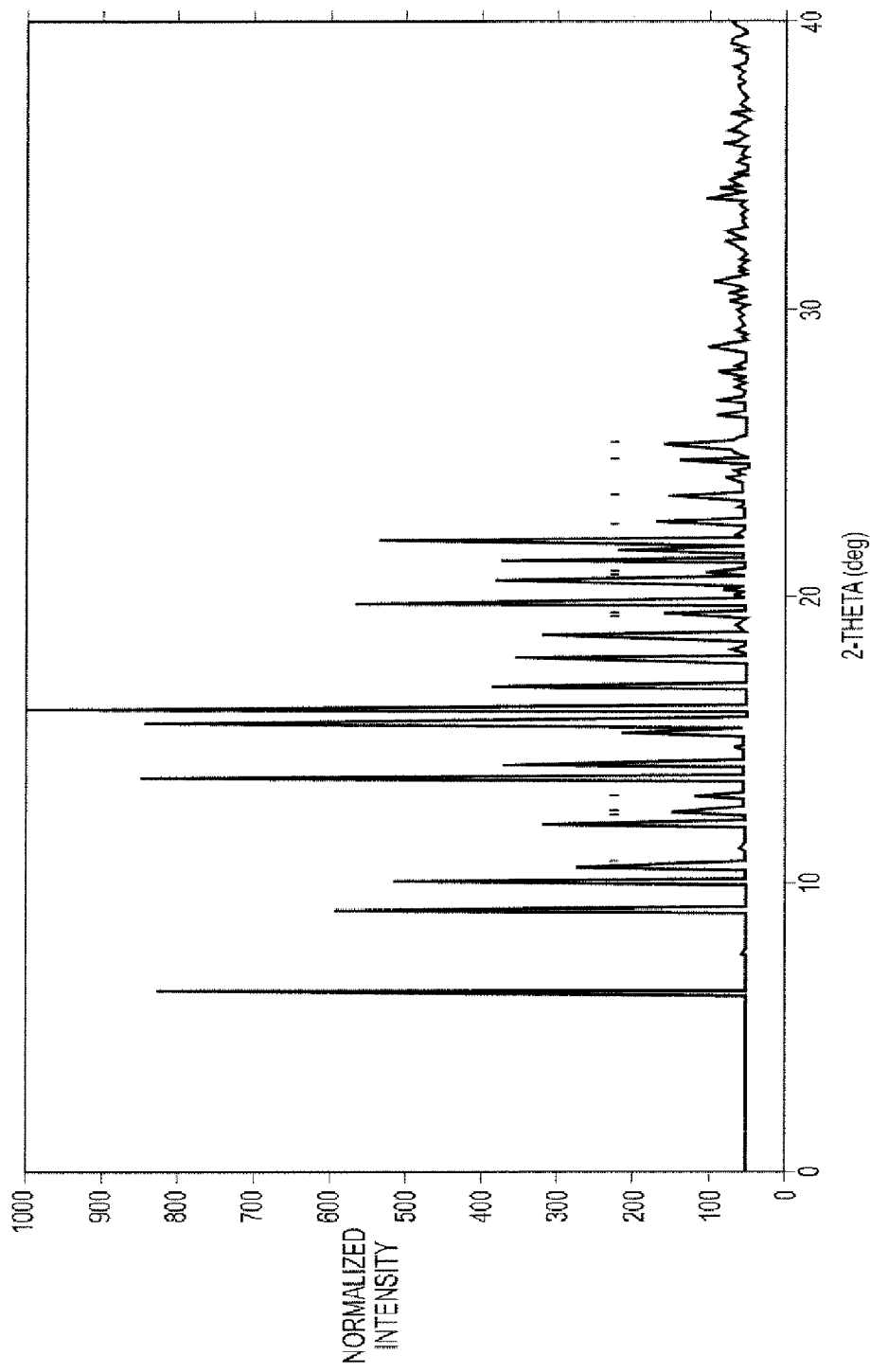

The colorless needle crystal with dimensions 0.22×0.14× 0.04 mm was mounted on a 0.2 nm nylon loop using very small amount of paratone oil. The single crystal structure, shown in FIG. 5-A, was determined using the procedure described above. Table 7 lists the crystal data and structure refinement parameters used to determine the single crystal structure of ER-111197 monohydrate. The structure was solved in the space group $P2_12_12_1$ (#19) by analysis of systematic absences. All non-hydrogen atoms were refined anisotropically. Hydrogens were calculated by geometrical methods and refined as a riding model. The Flack parameter was used to analyze the crystal. If the Flack parameter value is near zero, the absolute structure given by the structure element refinement is likely correct; if the value is near 1.0, then the inverted structure (the other enantiomer) is likely correct; if the value is near 0.5, the crystal is likely racemic. See Flack, H. D. *Acta Cryst.* A39, 1983, 876-881. The Flack parameter was refined to 0.3(13). The chirality of this compound was confirmed by its synthetic source. The crystal used for the diffraction study showed no decomposition during data collection. All drawing are done at 50% ellipsoids. FIG. 5-B is the crystal packing diagram along the a-axis which shows the hydrogen bonding within the crystal, dotted lines.

TABLE 7

Crystal data and structure refinement for ER-111197 monohydrate

| | |
|---|---|
| Empirical formula | $C_{40}H_{60}NO_{13}$ |
| Formula weight | 748.88 |
| Temperature | 193(2) K |
| Wavelength | 0.71073 Å |
| Crystal system | Orthorhombic |
| Space group | P2(1)2(1)2(1) |
| Unit cell dimensions | a = 9.907(3) Å    α = 90°. |
| | b = 11.212(4) Å   β = 90°. |
| | c = 34.483(13) Å  γ = 90°. |
| Volume | 3830(2) Å³ |
| Z | 4 |
| Density (calculated) | 1.299 Mg/m³ |
| Absorption coefficient | 0.096 mm$^{-1}$ |
| F(000) | 1616 |
| Crystal size | 0.22 × 0.14 × 0.04 mm³ |
| Theta range for data collection | 1.18 to 27.91°. |
| Index ranges | −13 <= h <= 12, −14 <= k <= 13, −42 <= l <= 45 |
| Reflections collected | 27456 |
| Independent reflections | 9109 [R(int) = 0.0720] |
| Completeness to theta = 27.91° | 99.8% |
| Absorption correction | None |
| Max. and min. transmission | 0.9962 and 0.9792 |
| Refinement method | Full-matrix least-squares on F² |
| Data/restraints/parameters | 9109/0/482 |
| Goodness-of-fit on F² | 0.893 |
| Final R indices [I > 2sigma(I)] | R1 = 0.0652, wR2 = 0.1453 |
| R indices (all data) | R1 = 0.1398, wR2 = 0.1659 |
| Absolute structure parameter | 0.3(13) |
| Largest diff. peak and hole | 0.911 and −0.346 e.Å$^{-3}$ |

C. Simulated X-Ray Powder Diffraction Spectrum of ER-111197 (Epi-C34 Diol) Monohydrate The simulated XRPD spectrum of ER-111197 generated from the single crystal data is shown in FIG. 5-C.

Example 6

Characterization of ER-809681 (epoxide)

A. Crystallization Procedure for the Generation of X-Ray Quality Crystal

ER-809681-00 (50 mg) was dissolved in dichloromethane (0.25 mL). Pentane (0.5 mL) was added. The solution was stirred until visually homogeneous. The solution was slowly evaporated at room temperature over 18 hours. Crystal suitable for X-ray crystallography study was collected by decanting supernatant liquid. The chemical structure of ER-809681 (epoxide) is shown below.

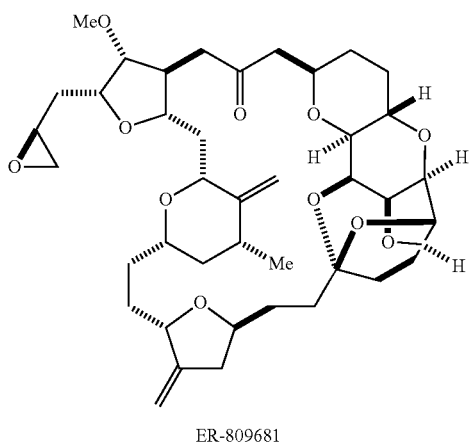

ER-809681

B. Single Crystal X-Ray Determination of ER-809681 (Epoxide)

Single crystal X-ray determination method varies from that described above and is detailed in the following section.

A colorless block crystal of $C_{40}H_{56}O_{11}$ having approximate dimensions of 0.30×0.10×0.10 mm was mounted on a glass fiber. The single crystal structure is shown in FIG. 6-A. All measurements were made on a Rigaku RAXIS RAPID imaging plate area detector with graphite monochromated Cu-K$_\alpha$ radiation. Indexing was performed from 3 oscillations that were exposed for 15 seconds. The crystal-to-detector distance was 127.40 mm. Cell constants and an orientation matrix for data collection corresponded to a primitive orthorhombic cell with dimensions: a=9.4700(3) Å; b=17.6327(5) Å; c=23.1790(6) Å; V=3870.47(19) Å$^3$. For Z=4 and F.W.=712.88, the calculated density was 1.223 g/cm$^3$. The systematic absences of: h00: h±2n; 0k0: k±2n; 00l: l±2n uniquely determine the space group to be: P2$_1$2$_1$2$_1$ (#19). The crystal packing diagram is shown in FIG. 6-B.

The data were collected at a temperature of 23±1° C. to a maximum 2θ value of 136.5°. A total of 30 oscillation images were collected. A sweep of data was done using ω scans from 80.0 to 260.0° in 30.0° step, at χ=54.0° and φ=15.0°. The exposure rate was 15.0 [sec./°]. A second sweep was performed using ω scans from 80.0 to 260.0° in 30.0° step, at χ=54.0° and φ=105.0°. The exposure rate was 15.0 [sec./°]. Another sweep was performed using ω scans from 80.0 to 260.0° in 30.0° step, at χ=54.0° and φ=180.0°. The exposure rate was 15.0 [sec./°]. Another sweep was performed using ω scans from 80.0 to 260.0° in 30.0° step, at χ=54.0° and φ=270.0°. The exposure rate was 15.0 [sec./°]. Another sweep was performed using ω scans from 80.0 to 260.0° in 30.0° step, at χ=0.0° and φ=0.0°. The exposure rate was 15.0 [sec./°]. The crystal-to-detector distance was 127.40 mm. Readout was performed in the 0.100 mm pixel mode.

Data Reduction: Of the 16412 reflections that were collected, 934 were unique ($R_{int}$=0.043); equivalent reflections were merged. The linear absorption coefficient, μ, for Cu-K$_\alpha$ radiation is 7.229 cm$^{-1}$. An empirical absorption correction was applied which resulted in transmission factors ranging from 0.748 to 0.930. The data were corrected for Lorentz and polarization effects.

Structure Solution and Refinement: The structure was solved by direct methods (SHELX97: Sheldrick, G. M. (1997)) and expanded using Fourier techniques. See DIRDIF99: Beurskens, P. T., Admiraal, G., Beurskens, G., Bosman, W. P., de Gelder, R., Israel, R. and Smits, J. M. M.(1999), "The DIRDIF-99 program system, Technical Report of the Crystallography Laboratory," University of Nijmegen, The Netherlands. The non-hydrogen atoms were refined anisotropically. Hydrogen atoms were refined using the riding model. The final cycle of full-matrix least-squares refinement on F$^2$, depicted as $\Sigma w(F_o^2-F_c^2)^2$ where w=least squares weights, was based on 7045 observed reflections and 461 variable parameters. It converged (largest parameter shift was 0.01 times its esd) with unweighted and weighted agreement factors of: R1=Σ||Fo|-|Fc||/Σ|Fo|=0.0630 and wR2=[Σ(w(F$_o^2$-F$_c^2$)$^2$)/Σw(F$_o^2$)$^2$]$^{1/2}$=0.2168.

The standard deviation of an observation of unit weight was 1.10, with the standard deviation of an observation of unit weight calculated as $[\Sigma w(F_o^2-F_o^2)^2/(N_o-N_v)]^{1/2}$, where: N$_o$=number of observations and N$_v$=number of variables. The maximum and minimum peaks on the final difference Fourier map corresponded to 0.20 and −0.28 e$^-$/Å$^3$, respectively.

Neutral atom scattering factors were taken from Cromer and Waber; "International Tables for X-ray Crystallography", Vol. IV, The Kynoch Press, Birmingham, England, Table 2.2 A (1974). Anomalous dispersion effects were included in F$_{calc}$ (see Ibers, J. A. & Hamilton, W. C.; Acta Crystallogr., 17, 781 (1964)), and the values for Δf' and Δf" were obtained from Creagh, D. C. & McAuley, W. J.; "International Tables for Crystallography", Vol C, (A. J. C. Wilson, ed.), Kluwer Academic Publishers, Boston, Table 4.2.6.8, pages 219-222 (1992). The values for the mass attenuation coefficients were taken from Creagh, D. C. & Hubbell, J. H.; "International Tables for Crystallography", Vol C, (A. J. C. Wilson, ed.), Kluwer Academic Publishers, Boston, Table 4.2.4.3, pages 200-206 (1992). All calculations were performed using the CrystalStructure crystallographic software package. See CrystalStructure 3.7.0: Crystal Structure Analysis Package, Rigaku and Rigaku/MSC (2000-2005), 9009 New Trails Dr. The Woodlands Tex. 77381 USA; and CRYSTALS Issue 10: Watkin, D. J., Prout, C. K. Carruthers, J. R. & Betteridge, P. W., Chemical Crystallography Laboratory, Oxford, UK. (1996). The exception to this was the calculations for refinement, which was performed using SHELX97: Sheldrick, G. M. (1997).

Crystal Data:

| | |
|---|---|
| Empirical Formula | $C_{40}H_{56}O_{11}$ |
| Formula Weight | 712.88 |
| Crystal Color, Habit | colorless, block |
| Crystal Dimensions | 0.30 × 0.10 × 0.10 mm |
| Crystal System | orthorhombic |
| Lattice Type | Primitive |
| Indexing Images | 3 oscillations @ 15.0 seconds |
| Detector Position | 127.40 mm |
| Pixel Size | 0.100 mm |
| Lattice Parameters | a = 9.4700(3) Å |
| | b = 17.6327(5) Å |
| | c = 23.1790(6) Å |
| | V = 3870.47(19) Å$^3$ |
| Space Group | P2$_1$2$_1$2$_1$(#19) |
| Z value | 4 |
| D$_{calc}$ | 1.223 g/cm$^3$ |
| F$_{000}$ | 1536.00 |
| μ(CuK$_\alpha$) | 7.229 cm$^{-1}$ |

Intensity Measurements:

| | |
|---|---|
| Diffractometer | Rigaku RAXIS-RAPID |
| Radiation | CuKα (λ = 1.54187 Å) graphite monochromated |
| Detector Aperture | 460 mm × 256 mm |
| Data Images | 30 exposures |
| ω oscillation Range (χ = 54.0, φ = 15.0) | 80.0-260.0° |

-continued

| | |
|---|---|
| Exposure Rate | 15.0 sec./° |
| ω oscillation Range (χ = 54.0, φ = 105.0) | 80.0-260.0° |
| Exposure Rate | 15.0 sec./° |
| ω oscillation Range (χ = 54.0, φ = 180.0) | 80.0-260.0° |
| Exposure Rate | 15.0 sec./° |
| ω oscillation Range (χ = 54.0, φ = 270.0) | 80.0-260.0° |
| Exposure Rate | 15.0 sec./° |
| ω oscillation Range (χ = 0.0, φ = 0.0) | 80.0-260.0° |
| Exposure Rate | 15.0 sec./° |
| Detector Position | 127.40 mm |
| Pixel Size | 0.100 mm |
| $2\theta_{max}$ | 136.5° |
| No. of Reflections Measured | Total: 16412 |
| | Unique: 37266 ($R_{int}$ = 0.043) |
| Corrections | Lorentz-polarization |
| | Absorption |
| | (trans. factors: 0.748-0.930) |

Structure Solution and Refinement:

| | |
|---|---|
| Structure Solution | Direct Methods (SHELX97) |
| Refinement | Full-matrix least-squares on $F^2$ |
| Function Minimized | $\Sigma w (F_o^2 - F_c^2)^2$ |
| Least Squares Weights | $w = 1/[\sigma^2(F_o^2) + (0.0877 \cdot P)^2 + 1.4243 \cdot P]$ |
| | where $P = (Max(F_o^2, 0) + 2F_c^2)/3$ |
| $2\theta_{max}$ cutoff | 136.5° |
| Anomalous Dispersion | All non-hydrogen atoms |
| No. Observations (All reflections) | 7045 |
| No. Variables | 461 |
| Reflection/Parameter Ratio | 15.28 |
| Residuals: R1 (I > 2.00σ(I)) | 0.0630 |
| Residuals: R (All reflections) | 0.1326 |
| Residuals: wR2 (All reflections) | 0.2168 |
| Goodness of Fit Indicator | 1.103 |
| Max Shift/Error in Final Cycle | 0.014 |
| Maximum peak in Final Diff. Map | 0.20 e⁻/Å³ |
| Minimum peak in Final Diff. Map | −0.28 e⁻/Å³ |

C. X-Ray Powder Diffraction (XRPD) Characterization of ER-809681 (Epoxide)

The XRPD collection method for this compound varies from the method described above only in the theta scan range, 2-70°. The XRPD pattern is shown in FIG. 6-C.

TABLE 8

XRPD Peaks of ER-809681 (epoxide)

| Position (2θ) | Rel. Int. (%) |
|---|---|
| 16.2 | 100.0 |
| 15.8 | 60.3 |
| 13.9 | 45.3 |
| 19.9 | 40.8 |
| 9.3 | 39.1 |
| 22.1 | 36.8 |
| 20.7 | 34.9 |
| 17.1 | 33.4 |
| 6.5 | 33.0 |
| 21.8 | 32.3 |
| 18.1 | 26.0 |
| 21.4 | 22.0 |
| 14.4 | 21.2 |
| 10.2 | 21.0 |
| 18.9 | 19.6 |
| 15.4 | 19.4 |
| 12.2 | 15.1 |

D. Simulated XRPD Spectrum

The simulated XRPD pattern generated from the single crystal data is shown in FIG. 6-D.

Example 7

Anti-Cancer Activity

The anti-cancer activity of the compounds described above, in the crystalline forms described, was determined using cell growth inhibition assays as described in Liu, J. et al. Anticancer Research, 27:1509-1511 (2007). The activity data in terms of $IC_{50}$ nM is described below in Table 9. MES-SA and MES-SA/Dx5-Rx1 uterine sarcoma, were obtained from the American Type Culture Collection and grown in the recommended conditions.

Cell Growth Inhibition Assays. Cells were seeded at 7.5× $10^3$ cells/well in 96-well plates in the recommended medium supplemented with 10% FBS and penicillin, streptomycin and L-glutamine. After 4 hours incubation, the test compound was added to each well to give a series of concentrations ranging from 0 to 10 μM. The cultures were incubated for 4 days at 37° C. The cell growth was determined using modifications (see Finlay G. J., et al. "A semiautomated microculture method for investigating growth inhibitory effects of cytotoxic compounds on exponentially growing carcinoma cells." Anal Biochem 139: 272-277, 1984) of a methylene blue-based microculture assay (See Towle M. J., et al. "In vitro and in vivo anticancer activities of synthetic macrocyclic ketone analogues of halichondrin B." Cancer Res 61: 1013-1021, 2001). The medium was removed and the cells were stained with 100 μl of methylene blue (500 μg/ml) for 45 min. After a wash with water, the stained cells were dissolved into 100 μl of sarcosine (1 mg/ml) for 90 min with gentle shaking. The plates were read at $A_{600}$-$A_{405}$.

Susceptibility of Compound to P-Glycoprotein-Mediated Multidrug Resistance (MDR). A pair of human uterine sarcoma cell lines was used: MES-SA, the MDR negative parental cell line, and Dx5-Rx1, a cell line derived from MES-SA after long term of exposure to doxorubicin. This subline expresses P-Glycoprotein at high levels. Both cell lines were seeded at 7.5×$10^3$ cells/well in McCoy's 5A supplemented with 10% FBS and penicillin, streptomycin and L-glutamine and cell growth was measured as above. The ratio of the $IC_{50}$ values obtained in the parental and resistant cell lines was termed fold resistance and provided an indication of compound susceptibility to P-glycoprotein-mediated MDR against the two cell lines were compared with each other.

TABLE 9

| Crystalline Form: | Example | Activity Data ($IC_{50}$ nM) MES-SA | Activity Data ($IC_{50}$ nM) Dx5-Rx1 | Ratio of DxR-Rx1/ MES-SA |
|---|---|---|---|---|
| ER-076349 monohydrate | 1 | 0.03 | 6.5 | 217 |
| ER-818906 (epi-C20 diol) mono-acetonitrile solvate | 2 | 0.96 | 75 | 78 |
| ER-819531 (epi-C23 diol) monohydrate | 3 | 1.4 | 330 | 236 |
| ER-820057 (epi-C23 amine) | 4 | 3.3 | 1000 | 303 |

TABLE 9-continued

| Crystalline Form: | Example | Activity Data (IC$_{50}$ nM) | | Ratio of DxR-Rx1/ |
| --- | --- | --- | --- | --- |
| | | MES-SA | Dx5-Rx1 | MES-SA |
| ER-111197 (epi-C34 diol) monohydrate | 5 | 0.23 | 43 | 186 |
| ER-809681 (epoxide) | 6 | 0.23 | 2.81 | 12 |

The claimed invention is:

1. A method of synthesizing:

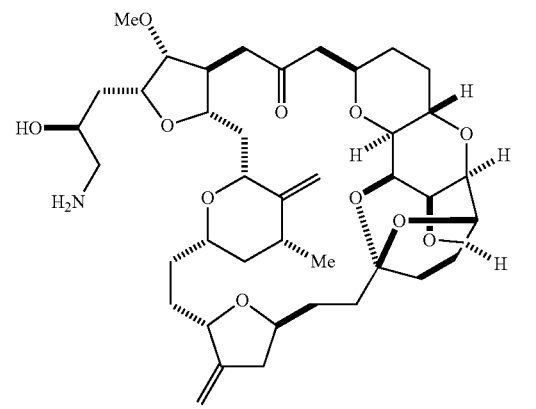

ER-086526

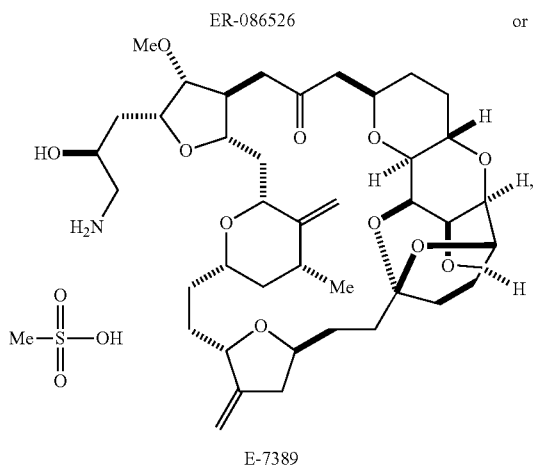

E-7389 said method comprising providing a crystalline monohydrate of the compound:

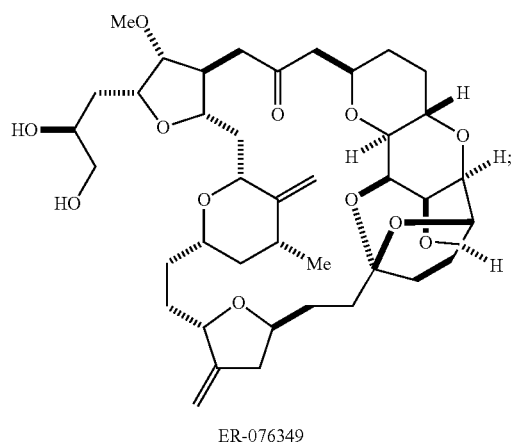

ER-076349 dissolving said crystalline monohydrate of ER-076349 in a solvent and tosylating ER-076349 to produce a compound having the formula:

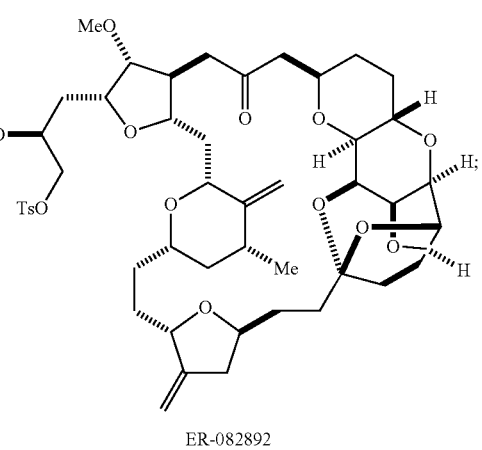

ER-082892 or reacting ER-082892 with ammonium hydroxide to produce in sequence a compound having the formula:

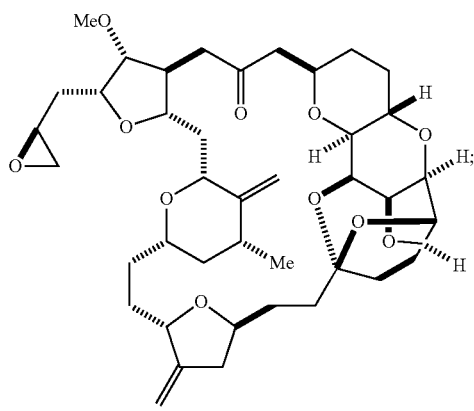

ER-809681 and ER-086526; and optionally salifying ER-086526 with methanesulfonic acid to produce E-7389.

2. The method of claim 1, wherein ER-082892 is produced by reacting tosyl anhydride with ER-076349.

3. The method of claim 1, wherein E-7389 is produced by salifying ER-086526 with methanesulfonic acid.

4. A method of synthesizing:

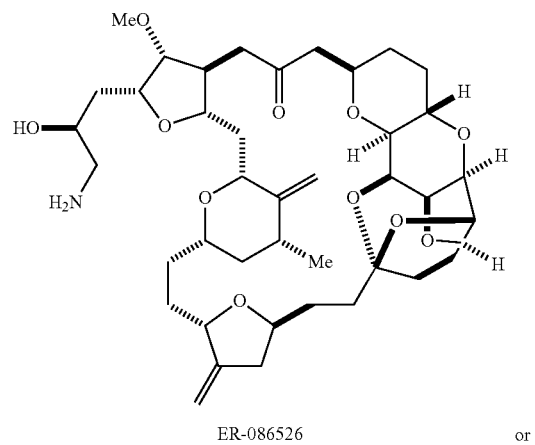

ER-086526 or

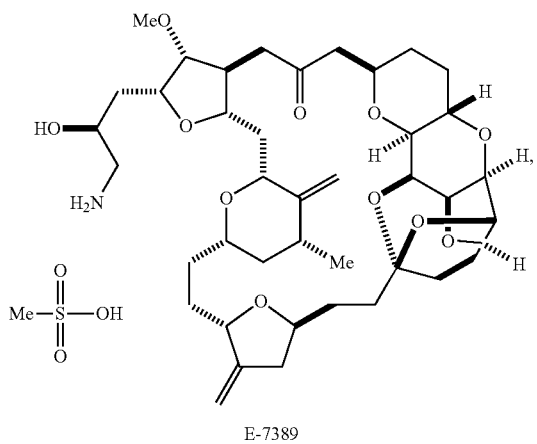

E-7389 said method comprising providing a crystalline form of the compound:

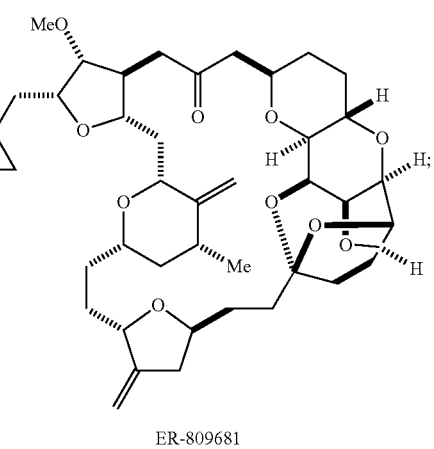

ER-809681 dissolving said crystalline form of ER-809681 in a solvent and reacting with ammonoim hydroxide to produce ER-086526; and optionally salifying ER-086526 with methanesulfonic acid to produce E-7389.

5. The method of claim 1, wherein said crystalline monohydrate of ER-076349 is characterized by a powder x-ray diffraction pattern having peaks at 9.3 °2Θ±0.2 °2Θ, 10.4 °2Θ±0.2 °2Θ, and 13.0 °2Θ±0.2 °2Θ.

6. The method of claim 4, wherein said crystalline form of ER-809681 is characterized by a powder x-ray diffraction pattern having peaks at 6.5 °2Θ±0.2 °2Θ, 9.3 °2Θ±0.2 °2Θ, and 17.1 °2Θ±0.2 °2Θ.

7. The method of claim 4, wherein E-7389 is produces by salifying ER-086526 with methanesulfonic acid.

* * * * *